(12) United States Patent
Hartz et al.

(10) Patent No.: US 7,030,145 B2
(45) Date of Patent: Apr. 18, 2006

(54) PYRIDINYL DERIVATIVES FOR THE TREATMENT OF DEPRESSION

(75) Inventors: Richard A. Hartz, Middletown, CT (US); Argyrios G. Arvanitis, Kennett Square, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 22 days.

(21) Appl. No.: 10/799,784

(22) Filed: Mar. 12, 2004

(65) Prior Publication Data

US 2004/0209917 A1 Oct. 21, 2004

Related U.S. Application Data

(60) Provisional application No. 60/464,058, filed on Apr. 18, 2003.

(51) Int. Cl.
C07D 211/72 (2006.01)
C07D 211/84 (2006.01)
A61K 31/44 (2006.01)

(52) U.S. Cl. ............... 514/349; 514/352; 546/293; 546/312; 546/297

(58) Field of Classification Search ......... 546/293, 546/312, 297; 514/349, 352
See application file for complete search history.

(56) References Cited

U.S. PATENT DOCUMENTS

2003/0096817 A1* 5/2003 Green et al. ............ 514/242

FOREIGN PATENT DOCUMENTS

| WO | WO 95/10506 | 4/1995 |
|---|---|---|
| WO | WO 95/33750 | 12/1995 |
| WO | WO 97/45421 | 12/1997 |
| WO | WO 98/03510 | 1/1998 |
| WO | WO 99/51608 | 10/1999 |
| WO | WO 00/53604 | 9/2000 |
| WO | WO 00/59888 | 10/2000 |
| WO | WO 01/53263 A1 | 7/2001 |
| WO | WO 01/62718 | 8/2001 |
| WO | WO 01/68614 A2 | 9/2001 |
| WO | WO 02/06242 A2 | 1/2002 |

OTHER PUBLICATIONS

Kehne, Current Drug Targets: CNS & Neurological Disorders, vol. 1(5), pp. 467-493, 2002.*

Dunn, A.J., et al., "Physiological and behavioral responses to corticotropin-releasing factor administration: is CRF a mediator of anxiety or stress responses?" Brain Research Reviews, 15, 1990, pp. 71-100.

Gulyas, J, et al., "Potent, structurally constrained agonists and competitive antagonists of corticotropin-releasing factor," Proc. Natl. Acad. Sci. USA, vol. 92, Nov. 1995, pp. 10575-10579.

McCarthy, et al., "Recent Advances with the CRF1 Receptor: Design of Small Molecule Inhibitors, Receptor Subtypes and Clinical Indications," Current Pharmaceutical Design, 1999, 5, pp. 289-315.

Holsboer, F., "The rationale for corticotropin-releasing hormone receptor (CRH-R) antagonists to treat depression and anxiety," Journal of Psychiatric Research, 33, 1999, pp. 181-214.

Banki, C.M., et al., "CSF corticotropin-releasing hormone and somatostatin in major depression: response to antidepressant treatment and relapse," European Neuropsycho- pharmacology, 2, 1992, pp. 107-113.

Webster, E.L., et al., "Corticotropin-Releasing Hormone and Inflammation," Annals New York Academy of Sciences, 840, 1998, pp. 21-32.

Gilligan, P.J., et al., "Corticotropin Releasing Factor (CRF) Receptor Modulators: Progress and Opportunities for New Therapeutic Agents," Journal of Medicinal Chemistry, vol. 43, No. 9, May 4, 2000, pp. 1641-1660.

McCarthy, J.R., et al., "Chapter 2. Recent Progress in Corticotropin-Releasing Factor Receptor Agents," Annual Reports in Medicinal Chemistry, vol. 34, 1999, pp. 11-20.

* cited by examiner

Primary Examiner—D. Margaret Seaman
(74) Attorney, Agent, or Firm—Shah Makujina; James Epperson

(57) ABSTRACT

The present invention relates to novel heterocyclic antagonists of Formula (I) and pharmaceutical compositions comprising said antagonists of the corticotropin releasing factor receptor ("CRF receptor")

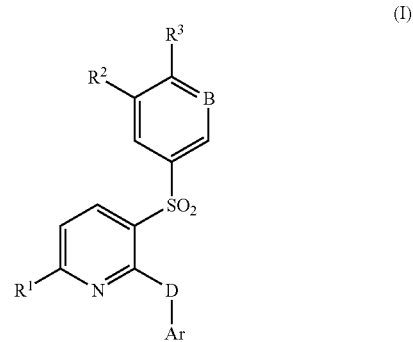

(I)

useful for the treatment of depression, anxiety, affective disorders, feeding disorders, post-traumatic stress disorder, headache, drug addiction, inflammatory disorders, drug or alcohol withdrawal symptoms and other conditions the treatment of which can be effected by the antagonism of the CRF-1 receptor.

11 Claims, No Drawings

PYRIDINYL DERIVATIVES FOR THE TREATMENT OF DEPRESSION

CROSS REFERENCE TO RELATED APPLICATION

This non-provisional application claims priority from provisional application U.S. Ser. No. 60/464,058 filed Apr. 18, 2003. The disclosure of this prior application is incorporated herein by reference in its entirety.

FIELD OF THE INVENTION

The present invention relates to antagonists and pharmaceutical compositions comprising said antagonists of the corticotropin releasing factor receptor ("CRF receptor") useful for the treatment of depression, anxiety, affective disorders, feeding disorders, post-traumatic stress disorder, headache, drug addiction, inflammatory disorders, drug or alcohol withdrawal symptoms and other conditions the treatment of which can be effected by the antagonism of the CRF-1 receptor.

BACKGROUND OF THE INVENTION

It has been shown that the neuropeptide, corticotropin releasing factor ("CRF"), acting through its binding to the CRF-1 receptor, is a primary mediator of stress- and anxiety-related physiological responses in humans and other mammals by stimulating ACTH secretion from the anterior pituitary gland. See A. J. Dunn, et al., *Brain Res. Rev.*, 15: 71–100 (1990). Antagonists of the CRF-1 receptor, both peptides (J. Gulyas, et al., *Proc. Natl. Acad. Sci. U.S.A.*, 92: 10575–10579 (1995) and small molecules (J. R. McCarthy, et al., *Curr. Pharm. Design,* 5: 289–315 (1999), have demonstrated the ability to ameliorate the effects of stressful stimuli in several animal models. In addition, marked elevations of CRF in cerebrospinal fluid have been detected in a large portion of individuals diagnosed with major depression and anxiety disorders, and the levels correlate with severity of the disease. See F. Holsboer, *J. Psychiatric Res.*, 33: 181–214 (1999). Following antidepressant treatment, the increased CRF levels observed in depressed patients were reduced. See C. M. Banki, et al., *Eur. Neuropsychopharmacol.,* 2: 107–113 (1992). CRF has also been shown to be a key mediator of several immune system functions through its effect on glucocorticoid plasma levels. See E. L. Webster, et al., *Ann. N.Y. Acad. Sci.,* 840: 21–32 (1998). Recent reviews of the activity of CRF-1 antagonists, P. J. Gilligan, et al., *J. Med. Chem.,* 43: 1641–1660 (2000) and J. R. McCarthy, et al., *Ann. Rep. Med. Chem.*, 34: 11–20 (1999) are incorporated herein by reference. There appears a need to discover novel small molecule CRF antagonists in order to treat a wide variety of human disorders including depression, anxiety, bipolar disorder, and other stress-related illnesses. See WO 95/10506, WO 95/33750, WO 97/45421, WO 98/03510, WO 99/51608, WO 00/59888, WO 00/53604, WO 01/53263, WO 01/62718, WO 01/68614, WO 02/06242 and PCT/US99/18707.

SUMMARY OF THE INVENTION

Thus according to a first embodiment of the first aspect of the present invention are provided compounds of Formula (I)

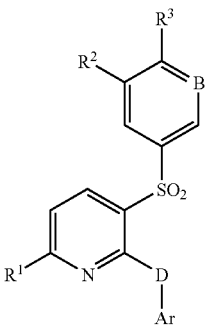

or pharmaceutically acceptable salts or solvates thereof, wherein
B is CH or N;
D is $CH_2$ or NH;
$R^1$ is selected from the group consisting of H, —CN, $C_{1-4}$ alkyl, $C_{3-7}$ cycloalkyl, $C_{2-4}$ alkenyl, $C_{2-4}$ alkynyl, $C_{1-4}$ alkoxy and $N(C_{1-4}$ alkyl$)_2$ optionally and independently substituted with 1 to 3 substituents selected from the group consisting of —CN, hydroxy, halo, $C_{1-4}$ haloalkyl and $C_{1-4}$ alkoxy;
$R^2$ is selected from the group consisting of H, halo, —CN, hydroxy, $C_{1-6}$ alkyl, $C_{2-6}$ alkenyl, $C_{2-6}$ alkynyl, $C_{3-7}$ cycloalkyl, $C_{1-6}$ alkoxy, $C_{1-6}$ haloalkyl, —$NR^4R^6$, —$C_{1-6}$alkyl$NR^4R^6$, —$C_{1-6}$alkyl$OR^6$, $CO_2R^6$, $O_2CR^6$, $COR^6$, $CONR^4R^6$, $NR^4CO_2R^6$, $NR^4SO_2R^6$, $NR^4COR^6$, $OCONR^4R^6$ and $NR^4CONR^5R^6$;
optionally and independently substituted with 1 to 3 substituents selected from the group consisting of —CN, hydroxy, halo, $C_{1-4}$ haloalkyl, $C_{1-4}$ alkoxy, $CO_2C_{1-4}$ alkyl or phenyl; or
$R^2$ is morpholinyl, thiomorpholinyl, piperadinyl, piperazinyl, phenyl, pyridyl, pyrimidinyl, triazinyl, quinolinyl, isoquinolinyl, thienyl, imidazolyl, thiazolyl, indolyl, pyrrolyl, pyrrolidinyl, dihydroimidazolyl, oxazolyl, benzofuranyl, benzothienyl, benzothiazolyl, benzoxazolyl, isoxazolyl, triazolyl, tetrazolyl and indazolyl, independently and optionally substituted with 1 to 4 substituents selected from the group consisting of H, $C_{1-6}$ alkyl, $C_{1-4}$ alkoxy-$C_{1-4}$ alkyl, $C_{3-6}$ cycloalkyl, —$OR^4$, halo, $C_{1-4}$ haloalkyl, —CN, SH, —$S(O)_2R^5$, —$COR^4$, —$CO_2R^4$, —$OC(O)R^5$, —$N(COR^4)_2$, —$NR^4R^7$ and —$CONR^4R^7$, —$NR^4COR^5$, $NR^4SO_2R^5$, $NR^4CONR^5R^7$ or $NR^4CO_2R^5$;
$R^3$ is selected from the group consisting of H, halo, —CN, hydroxy, $C_{1-6}$ alkyl, $C_{2-6}$ alkenyl, $C_{2-6}$ alkynyl, $C_{3-7}$ cycloalkyl, $C_{1-6}$ alkoxy, $C_{1-6}$ haloalkyl, —$NR^4R^6$, —$C_{1-6}$alkyl$NR^4R^6$, —$C_{1-6}$alkyl$OR^6$, $CO_2R^6$, $O_2CR^6$, $COR^6$, $CONR^4R^6$, $NR^4CO_2R^6$, $NR^4SO_2R^6$, $NR^4COR^6$, $OCONR^4R^6$, and $NR^4CONR^5R^6$;
optionally and independently substituted with 1 to 3 substituents selected from the group consisting of —CN, hydroxy, halo, $C_{1-4}$ haloalkyl, $C_{1-4}$ alkoxy, $CO_2C_{1-4}$ alkyl, phenyl or naphthl; or
$R^3$ is morpholinyl, thiomorpholinyl, piperadinyl, piperazinyl, phenyl, pyridyl, pyrimidinyl, triazinyl, quinolinyl, isoquinolinyl, thienyl, imidazolyl, thiazolyl, indolyl, pyrrolyl, pyrrolidinyl, dihydroimidazolyl, oxazolyl, benzofuranyl, benzothienyl, benzothiazolyl, benzoxazolyl, isoxazolyl, triazolyl, tetrazolyl and indazolyl, independently and optionally substituted with 1 to 4 substituents selected from the group consisting of H, $C_{1-6}$ alkyl, $C_{3-6}$ cycloalkyl, $C_{1-4}$ alkoxy-$C_{1-4}$ alkyl, —$OR^4$, halo, $C_{1-4}$ haloalkyl, —CN, SH, —$S(O)_2R^5$, —$COR^4$, —$CO_2R^4$, —OC(O)$R^5$, —N(COR$^4$)$_2$, —NR$^4R^7$ and —CONR$^4R^7$, —NR$^4$COR$^5$, NR$^4$SO$_2$R$^5$, NR$^4$CONR$^5$R$^7$ or NR$^4$CO$_2$R$^5$;

Ar is selected from the group consisting of phenyl, indanyl, indenyl, pyridyl, pyrimidinyl, triazinyl, furanyl, quinolinyl, isoquinolinyl, thienyl, imidazolyl, thiazolyl, indolyl, pyrrolyl, pyrrolidinyl, dihydroimidazolyl, oxazolyl, benzofuranyl, benzothienyl, benzothiazolyl, benzoxazolyl, isoxazolyl, triazolyl, tetrazolyl, indazolyl, indolinyl, benzoxazolin-2-on-yl, benzodioxolanyl and benzodioxane, independently and optionally substituted with 1 to 4 substituents selected from the group consisting of H, $C_{1-6}$ alkyl, $C_{3-6}$ cycloalkyl, $C_{1-4}$ alkoxy-$C_{1-4}$ alkyl, —$OR^4$, halo, $C_{1-4}$ haloalkyl, —CN, —$NO_2$, SH, —$S(O)_2R^5$, —$COR^4$, —$CO_2R^4$, —OC(O)$R^5$, —N(COR$^4$)$_2$, —NR$^4R^7$ and —CONR$^4R^7$, —NR$^4$COR$^5$, NR$^4$SO$_2$R$^5$, NR$^4$CONR$^5$R$^7$, and NR$^4$CO$_2$R$^5$;

$R^4$, $R^5$ and $R^7$ are independently selected from the group consisting of H, $C_{1-6}$ alkyl, $C_{3-6}$ cycloalkyl, $C_{3-6}$ cycloalkyl-$C_{3-6}$ alkyl, $C_{1-2}$ alkoxy-$C_{1-4}$ alkyl and $C_{1-4}$ haloalkyl; and $R^6$ is selected from the group consisting of H, $C_{1-6}$ alkyl, $C_{3-6}$ cycloalkyl, $C_{3-6}$ cycloalkyl-$C_{1-6}$ alkyl, $C_{1-2}$ alkoxy-$C_{1-2}$ alkyl, $C_{1-4}$ haloalkyl, phenyl and $C_{1-6}$ alkyl-phenyl.

According to another embodiment of the first aspect of the present invention are provided compounds of Formula (I) according to the first embodiment of the first aspect wherein B is CH.

According to another embodiment of the first aspect of the present invention are provided compounds of Formula (I) according to the first embodiment of the first aspect wherein D is NH.

According to another embodiment of the first aspect of the present invention are provided compounds of Formula (I) according to the first embodiment of the first aspect wherein $R^1$ is $C_{1-4}$ alkyl.

According to another embodiment of the first aspect of the present invention are provided compounds of Formula (I) according to the first embodiment of the first aspect wherein $R^2$ is H, halo, hydroxy, $C_{1-6}$ alkyl, $C_{1-6}$ alkoxy, morpholinyl, piperazinyl or phenyl.

According to another embodiment of the first aspect of the present invention are provided compounds of Formula (I) according to the first embodiment of the first aspect wherein $R^3$ is H, halo, —CN, hydroxy, $C_{1-6}$ alkyl, $C_{2-6}$ alkynyl, $C_{1-6}$ alkoxy, $C_{1-6}$ haloalkyl, —NR$^4R^6$, morpholinyl, piperazinyl or phenyl.

According to another embodiment of the first aspect of the present invention are provided compounds of Formula (I) according to the first embodiment of the first aspect wherein Ar is phenyl, pyridyl, pyrimidinyl, imidazolyl, thiazolyl, pyrrolidinyl, dihydroimidazolyl independently and optionally substituted with 1 to 4 substituents selected from the group consisting of H, $C_{1-6}$ alkyl, —$OR^4$, halo, —CN, —$NO_2$, —$CO_2R^4$.

According to another embodiment of the first aspect of the present invention are provided compounds of Formula (I) according to the first embodiment of the first aspect wherein $R^4$, $R^5$ and $R^7$ are independently H or $C_{1-6}$ alkyl.

According to another embodiment of the first aspect of the present invention are provided compounds of Formula (I) according to the first embodiment of the first aspect wherein $R^6$ is H.

According to another embodiment of the first aspect of the present invention are provided compounds of Formula (I) according to the first embodiment of the first aspect wherein B is CH; D is NH; $R^1$ is $C_{1-4}$ alkyl; $R^2$ is H, halo, hydroxy, $C_{1-6}$ alkyl, $C_{1-6}$ alkoxy, morpholinyl, piperazinyl or phenyl; $R^3$ is H, halo, —CN, hydroxy, $C_{1-6}$ alkyl, $C_{2-6}$ alkynyl, $C_{1-6}$ alkoxy, $C_{1-6}$ haloalkyl, —NR$^4R^6$, morpholinyl, piperazinyl or phenyl; Ar is phenyl, pyridyl, pyrimidinyl, imidazolyl, thiazolyl, pyrrolidinyl, dihydroimidazolyl independently and optionally substituted with 1 to 4 substituents selected from the group consisting of H, $C_{1-6}$ alkyl, —$OR^4$, halo, —CN, —$NO_2$, —$CO_2R^4$; $R^4$, $R^5$ and $R^7$ are independently H or $C_{1-6}$ alkyl; and $R^6$ is H.

According to another embodiment of the first aspect of the present invention are provided compounds of the present invention selected from the group consisting of {3-[4-(2-Methoxybenzyloxy)-benzenesulfonyl]-6-methylpyridin-2-yl}-(4-methoxy-2-methylphenyl)-amine;

(2-Chloro-5-fluoro-4-methoxyphenyl)-{3-[4-(2-methoxybenzyloxy)-benzenesulfonyl]-6-methylpyridin-2-yl}-amine;

2-Chloro-5-fluoro-N$^1$-{3-[4-(2-methoxybenzyloxy)-benzenesulfonyl]-6-methylpyridin-2-yl}-N$^4$,N$^4$-dimethylbenzene-1,4-diamine;

(4,5-Dimethoxy-2-methylphenyl)-{3-[4-(2-methoxybenzyloxy)-benzenesulfonyl]-6-methylpyridin-2-yl}-amine;

(2-Chloro-4-difluoromethoxyphenyl)-{3-[4-(2-methoxybenzyloxy)-benzenesulfonyl]-6-methylpyridin-2-yl}-amine;

(2-Chloro-4,5-dimethoxyphenyl)-{3-[4-(2-methoxybenzyloxy)-benzenesulfonyl]-6-methylpyridin-2-yl}-amine;

(2-Chloro-4-methanesulfonylphenyl)-{3-[4-(2-methoxybenzyloxy)-benzenesulfonyl]-6-methylpyridin-2-yl}-amine;

5-Chloro-2-{3-[4-(2-methoxybenzyloxy)-benzenesulfonyl]-6-methylpyridin-2-ylamino}-benzonitrile;

[3-(4-Methoxybenzenesulfonyl)-6-methylpyridin-2-yl]-(2,4,6-trimethylphenyl)-amine;

4-[6-Methyl-2-(2,4,6-trimethylphenylamino)-pyridine-3-sulfonyl]-phenol;

[3-(4-Benzyloxybenzenesulfonyl)-6-methylpyridin-2-yl]-(2,4,6-trimethylphenyl)-amine;

[3-(4-Ethoxybenzenesulfonyl)-6-methylpyridin-2-yl]-(2,4,6-trimethylphenyl)-amine;

[3-(4-Allyloxybenzenesulfonyl)-6-methylpyridin-2-yl]-(2,4,6-trimethylphenyl)-amine;

4-{4-[6-Methyl-2-(2,4,6-trimethylphenylamino)-pyridine-3-sulfonyl]-phenoxy}-butyronitrile;

5-{4-[6-Methyl-2-(2,4,6-trimethylphenylamino)-pyridine-3-sulfonyl]-phenoxy}-pentanenitrile;

3-{4-[6-Methyl-2-(2,4,6-trimethylphenylamino)-pyridine-3-sulfonyl]-phenoxy}-propan-1-ol;

{4-[6-Methyl-2-(2,4,6-trimethylphenylamino)-pyridine-3-sulfonyl]-phenoxy}-acetic acid ethyl ester;

2-{4-[6-Methyl-2-(2,4,6-trimethylphenylamino)-pyridine-3-sulfonyl]-phenoxy}-butyric acid methyl ester;

{6-Methyl-3-[4-(pyridin-2-ylmethoxy)-benzenesulfonyl]-pyridin-2-yl}-(2,4,6-trimethylphenyl)-amine;

{3-[4-(2,6-Dichloropyridin-4-ylmethoxy)-benzenesulfonyl]-6-methylpyridin-2-yl}-(2,4,6-trimethylphenyl)-amine;

{6-Methyl-3-[4-(2-methylthiazol-4-ylmethoxy)-benzenesulfonyl]-pyridin-2-yl}-(2,4,6-trimethylphenyl)-amine;

{3-[4-(4-Fluorobenzyloxy)-benzenesulfonyl]-6-methylpyridin-2-yl}-(2,4,6-trimethylphenyl)-amine;

4-{4-[6-Methyl-2-(2,4,6-trimethylphenylamino)-pyridine-3-sulfonyl]-phenoxymethyl}-benzonitrile;

3-{4-[6-Methyl-2-(2,4,6-trimethylphenylamino)-pyridine-3-sulfonyl]-phenoxymethyl}-benzonitrile;

3-{4-[6-Methyl-2-(2,4,6-trimethylphenylamino)-pyridine-3-sulfonyl]-phenoxymethyl}-benzoic acid methyl ester;

{3-[4-(3-Methoxybenzyloxy)-benzenesulfonyl]-6-methylpyridin-2-yl}-(2,4,6-trimethylphenyl)-amine;

{3-[4-(2-Methoxybenzyloxy)-benzenesulfonyl]-6-methylpyridin-2-yl}-(2,4,6-trimethylphenyl)-amine;

2-{4-[6-Methyl-2-(2,4,6-trimethylphenylamino)-pyridine-3-sulfonyl]-phenoxymethyl}-benzonitrile;

{6-Methyl-3-[4-(2-nitrobenzyloxy)-benzenesulfonyl]-pyridin-2-yl}-(2,4,6-trimethylphenyl)-amine;

{3-[4-(3,5-Dimethoxybenzyloxy)-benzenesulfonyl]-6-methylpyridin-2-yl}-(2,4,6-trimethylphenyl)-amine;

{3-[4-(2,5-Dimethoxybenzyloxy)-benzenesulfonyl]-6-methyl-pyridin-2-yl}-(2,4,6-trimethylphenyl)-amine;

{3-[4-(2,3-Dimethoxybenzyloxy)-benzenesulfonyl]-6-methyl-pyridin-2-yl}-(2,4,6-trimethylphenyl)-amine;

{3-[4-(2,3-Difluorobenzyloxy)-benzenesulfonyl]-6-methyl-pyridin-2-yl}-(2,4,6-trimethylphenyl)-amine;

{3-[4-(2-Fluoro-6-nitrobenzyloxy)-benzenesulfonyl]-6-methyl-pyridin-2-yl}-(2,4,6-trimethylphenyl)-amine;

1-(4-Fluoro-3-{4-[6-methyl-2-(2,4,6-trimethylphenylamino)-pyridine-3-sulfonyl]-phenoxymethyl}-phenyl)-ethanone;

{3-[4-(2,6-Dimethylbenzyloxy)-benzenesulfonyl]-6-methylpyridin-2-yl}-(2,4,6-trimethylphenyl)-amine;

[3-(3-Chloro-4-fluorobenzenesulfonyl)-6-methylpyridin-2-yl]-(2,4,6-trimethylphenyl)-amine;

[3-(3,4-Dimethylbenzenesulfonyl)-6-methylpyridin-2-yl]-(2,4,6-trimethylphenyl)-amine;

[3-(3,4-Dimethoxybenzenesulfonyl)-6-methylpyridin-2-yl]-(2,4,6-trimethylphenyl)-amine;

[3-(3,4-Dichlorobenzenesulfonyl)-6-methylpyridin-2-yl]-(2,4,6-trimethylphenyl)-amine;

[6-Methyl-3-(toluene-4-sulfonyl)-pyridin-2-yl]-(2,4,6-trimethylphenyl)-amine;

[3-(4-Ethylbenzenesulfonyl)-6-methylpyridin-2-yl]-(2,4,6-trimethylphenyl)-amine;

[3-(4-Isopropylbenzenesulfonyl)-6-methylpyridin-2-yl]-(2,4,6-trimethylphenyl)-amine;

[6-Methyl-3-(4-trifluoromethoxybenzenesulfonyl)-pyridin-2-yl]-(2,4,6-trimethylphenyl)-amine;

[3-(4-Fluorobenzenesulfonyl)-6-methylpyridin-2-yl]-(2,4,6-trimethylphenyl)-amine;

[3-(4-Bromobenzenesulfonyl)-6-methylpyridin-2-yl]-(2,4,6-trimethylphenyl)-amine;

[3-(4-Ethynylbenzenesulfonyl)-6-methylpyridin-2-yl]-(2,4,6-trimethylphenyl)-amine;

[3-(Biphenyl-4-sulfonyl)-6-methylpyridin-2-yl]-(2,4,6-trimethylphenyl)-amine;

[3-(2'-Methoxybiphenyl-4-sulfonyl)-6-methylpyridin-2-yl]-(2,4,6-trimethylphenyl)-amine;

{4-[6-Methyl-2-(2,4,6-trimethylphenylamino)-pyridine-3-sulfonyl]-phenyl}-methanol;

(6-Methyl-3-{4-[(2,4,6-trimethylphenylamino)-methyl]-benzenesulfonyl}-pyridin-2-yl)-(2,4,6-trimethylphenyl)-amine;

4-[6-Methyl-2-(2,4,6-trimethylphenylamino)-pyridine-3-sulfonyl]-benzaldehyde;

{4-[6-Methyl-2-(2,4,6-trimethylphenylamino)-pyridine-3-sulfonyl]-phenyl}-phenyl-methanol;

{4-[6-Methyl-2-(2,4,6-trimethylphenylamino)-pyridine-3-sulfonyl]-phenyl}-phenyl-methanone;

Acetic acid 4-[6-methyl-2-(2,4,6-trimethylphenylamino)-pyridine-3-sulfonyl]-benzyl ester;

[3-(3-Methoxybenzenesulfonyl)-6-methylpyridin-2-yl]-(2,4,6-trimethylphenyl)-amine;

3-[6-Methyl-2-(2,4,6-trimethylphenylamino)-pyridine-3-sulfonyl]-phenol;

[3-(3-Ethoxybenzenesulfonyl)-6-methylpyridin-2-yl]-(2,4,6-trimethylphenyl)-amine;

[3-(3-Allyloxybenzenesulfonyl)-6-methylpyridin-2-yl]-(2,4,6-trimethylphenyl)-amine;

[3-(3-Benzyloxybenzenesulfonyl)-6-methylpyridin-2-yl]-(2,4,6-trimethylphenyl)-amine;

{3-[3-(4-Fluorobenzyloxy)-benzenesulfonyl]-6-methylpyridin-2-yl}-(2,4,6-trimethylphenyl)-amine;

{3-[3-(3-Methoxybenzyloxy)-benzenesulfonyl]-6-methylpyridin-2-yl}-(2,4,6-trimethylphenyl)-amine;

{3-[3-(3,5-Dimethoxybenzyloxy)-benzenesulfonyl]-6-methylpyridin-2-yl}-(2,4,6-trimethylphenyl)-amine;

{3-[3-(6-Chloropyridin-3-ylmethoxy)-benzenesulfonyl]-6-methylpyridin-2-yl}-(2,4,6-trimethylphenyl)-amine;

{3-[3-(2,6-Dichloropyridin-4-ylmethoxy)-benzenesulfonyl]-6-methylpyridin-2-yl}-(2,4,6-trimethylphenyl)-amine;

(2,4-Dimethylphenyl)-[3-(4-ethylbenzenesulfonyl)-6-methylpyridin-2-yl]-amine;

[3-(4-Ethylbenzenesulfonyl)-6-methylpyridin-2-yl]-(4-methoxy-2-methylphenyl)-amine;

(2,4-Dimethoxyphenyl)-[3-(4-ethylbenzenesulfonyl)-6-methylpyridin-2-yl]-amine;

(2-Chloro-4-methoxyphenyl)-[3-(4-ethylbenzenesulfonyl)-6-methylpyridin-2-yl]-amine; and

[3-(4-Ethylbenzenesulfonyl)-6-methylpyridin-2-yl]-(2,4,5-trimethylphenyl)-amine.

According to a second aspect of the present invention are provided pharmaceutical compositions comprising compounds of the present invention.

According to various embodiments of a third aspect of the present invention are provided methods of treating depression, anxiety, affective disorders, post-traumatic stress disorder, post-operative stress, headache, drug addiction, eating disorders and obesity, sudden death due to cardiac disorders, iritable bowel syndrome, hypertension, syndrome X, inflammatory disorders, stress-induced immune suppression, infertility, stress-induced insomnia and other sleep disorders, seizures, epilepsy, stroke and cerebral ischemia, traumatic brain injury, yet other disorders requiring neuroprotection, drug or alcohol withdrawal symptoms, other disorders including tachycardia, congestive heart failure, osteoporosis, premature birth, psychosocial dwarfism, ulcers, diarrhea, post-operative ileus and yet other conditions the treatment of which can be effected by the antagonism of the CRF-1 receptor by the administration of pharmaceutical compositions comprising compounds of the present invention as described herein.

Other embodiments of the present invention may comprise a suitable combination of two or more of the embodiments and/or aspects disclosed herein.

Yet other embodiments and aspects of the invention will be apparent according to the description provided below.

DETAILED DESCRIPTION OF THE INVENTION

Synthesis

The novel compounds of the present invention may be prepared in a number of ways well known to one skilled in the art of organic synthesis. The compounds of the present invention can be synthesized using the methods described below, together with synthetic methods known in the art of organic chemistry, or variations thereon as appreciated by those skilled in the art. Preferred methods include, but are not limited to, those described below. All references cited herein are hereby incorporated in their entirety herein by reference.

The novel compounds of this invention may be prepared using the reactions and techniques in this section. The reactions are performed in solvents appropriate to the reagents and materials employed and suitable for the transformation being effected. Also, in the description of the synthetic methods described below, it is to be understood that all proposed reaction conditions, including choice of solvents, reaction temperature, duration of the experiment and workup procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents which are compatible with the reaction conditions will be readily apparent to one skilled in the art and alternate methods must then be used.

Synthesis of various arylsulfonyl pyridines is outlined below. 6-Methyl-2-pyridone 2 was iodinated selectively at the 3-position to give 3 using an iodinating agent such as $I_2$, N-iodosuccinimide, Cl—I etc. in a solvent mixture such as dichloromethane-water, acetonitrile, methanol dioxane or tetrahydrofuran in the presence of an acid scavenger such as $NaHCO_3$. 3-Iodo-6-methyl-2-pyridone 3 was coupled with an arylthiophenol in the presence of a metal, metal hydride, alkoxide, hydroxide or carbonate base such as Na, NaH, NaOH, NaOMe, $Na_2CO_3$, K, KH, KOH, $K_2CO_3$, etc and a copper salt such as CuI, CuBr and CuCl in an organic solvent to give the coupled product 4. 2-Pyridone 4 was converted to the corresponding 2-chloropyridine with a chlorinating agent such as $POCl_3$, $(COCl)_2$, $SOCl_2$ to give the corresponding 2-chloropyridine 5. The arylsulfide was oxidized to the corresponding sulfone 6 via the action of an oxidizing agent such as a peroxide.

Scheme 1

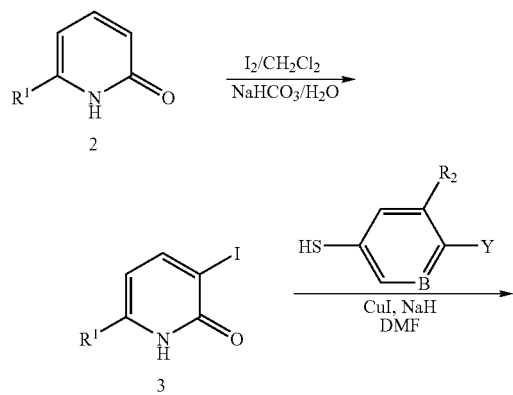

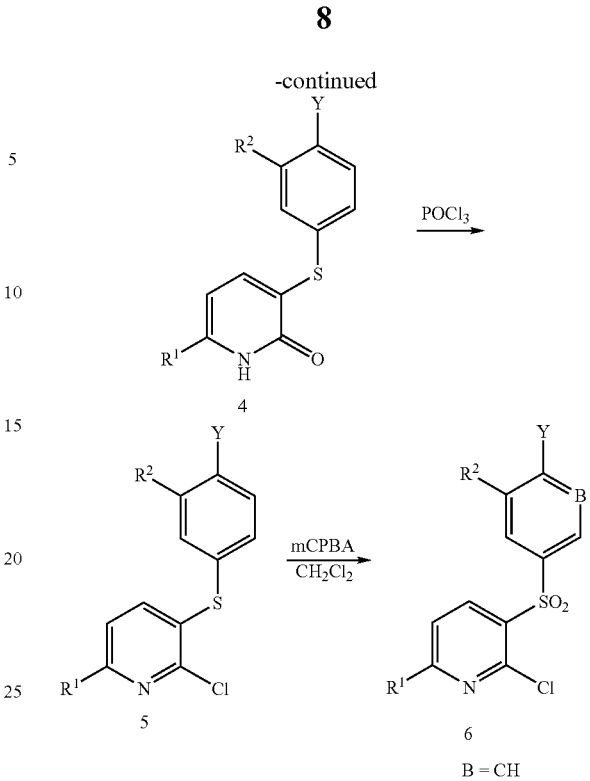

Compounds of formula 1 can be prepared from adducts 6 by the methods outlined in Scheme 2. Deprotection of the methoxy group can be effected upon treatment of 6 with $BBr_3$, HBr, LiI in collidine, or related reagents known to those skilled in the art of organic chemistry as described in *Protective Groups in Organic Synthesis*, (Greene, Wuts; 3$^{rd}$ ed., 1999, John Wiley & Sons, Inc.). When HBr is used, adducts 7 are formed. An intermediate leading to compounds of formula 1 wherein $R_3$ is joined to the aryl group with an oxygen atom can be prepared by subjecting compounds 7 to alkylation conditions. The reaction is carried out in the presence of an alkylating agent such as an alkyl halide, alkyl mesylate, alkyl tosylate or alkyl triflate in the presence of a base such as $K_2CO_3$, $Na_2CO_3$, $Et_3N$, i-$Pr_2NEt$ or alkali metal alkoxides (preferably KOt-Bu) in a polar organic solvent such as acetone, acetonitrile, dimethoxyethane, dioxane, chloroform or methylene chloride (preferably acetonitrile). Optionally, the reaction can be promoted by the addition of a salt such as KI to form compounds 8. Alternatively, this alkylation reaction can be effected using conditions described by Mitsunobu (Mitsunobu, O., *Synthesis*, 1981, 1). Compounds of formula 1 where B=CH and D=NH can be formed from adducts 8 using conditions described by Wagaw and Buchwald (*J. Org. Chem.*, 1996, 61, 7240–7241).

Alternatively, compounds of formula 1 where B=CH and D=NH can be prepared from adducts 6 in three steps by treatment of 6 with an aniline in the presence or absence of either a transition metal catalyst (such as copper iodide), acid or base and in the presence or absence of solvent at temperatures ranging from 22° C. to 210° C. to form 9. If the reaction is carried out in the presence of a base, bases such as $Et_3N$, i-$Pr_2NEt$, $K_2CO_3$ or $Na_2CO_3$ are used. If the reaction is carried out in the presence of acid, acids such as organic acids are used (preferably p-TsOH). Solvents such as ethylene glycol can be used for this reaction. Deprotection of the methoxy group can be effected upon treatment of 9 with BBr$_3$, HBr, LiI in collidine (preferably LiI in collidine) or related reagents known to those skilled in the art of organic chemistry as described in *Protective Groups in Organic Synthesis*, (Greene, Wuts; 3$^{rd}$ ed., 1999, John Wiley & Sons, Inc.). Intermediates 10 can be alkylated or acetylated to form compounds of formula 1. For alkylation adducts, the reaction is carried out in the presence of an alkylating agent such as an alkyl halide, alkyl mesylate, alkyl tosylate or alkyl triflate in the presence of a base such as K$_2$CO$_3$, Na$_2$CO$_3$, Et$_3$N, i-Pr$_2$NEt or alkali metal alkoxides (preferably K$_2$CO$_3$) in a polar organic solvent such as acetone, acetonitrile, dimethoxyethane, dioxane, chloroform or methylene chloride (preferably acetonitrile). Optionally, the reaction can be promoted by the addition of a salt such as KI or NaI to form compounds 1. Alternatively, this alkylation reaction can be effected using conditions described by Mitsunobu (Mitsunobu, O., *Synthesis*, 1981, 1). For acylation adducts, compounds 10 are subjected to acylating reagents, such as symmetrical anhydrides, mixed anhydrides, acid halides or esters in the presence of a base, such as, but not limited to, Et$_3$N or i-Pr$_2$NEt in the presence or absence of solvent. Alternatively, a carboxylic acid may be coupled with 10 to form an adduct of formula 1 where R$_3$ is an ester using coupling reagents such as, but not limited to, EDC, DCC, BOP, PyBOP and pentafluorophenol in the presence of an organic solvent such as methylene chloride or DMF.

In the case where Y=CHO (9a) the formyl group may be converted to the corresponding arylketone 1 by addition of organometallic reagents followed by oxidation of the resulting alcohol (Scheme 3). In the case where Y=Br, 9b (R=Br) may be coupled with various boronic acids in the presence of barium hydroxide and a palladium catalyst to give the corresponding biaryl adducts of formula 1.

Scheme 3

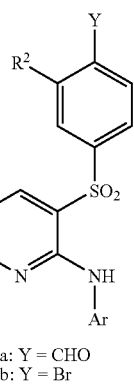
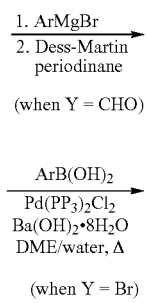

9a: Y = CHO
9b: Y = Br

1. ArMgBr
2. Dess-Martin periodinane (when Y = CHO)

ArB(OH)$_2$
Pd(PP$_3$)$_2$Cl$_2$
Ba(OH)$_2$•8H$_2$O
DME/water, Δ

(when Y = Br)

Scheme 2

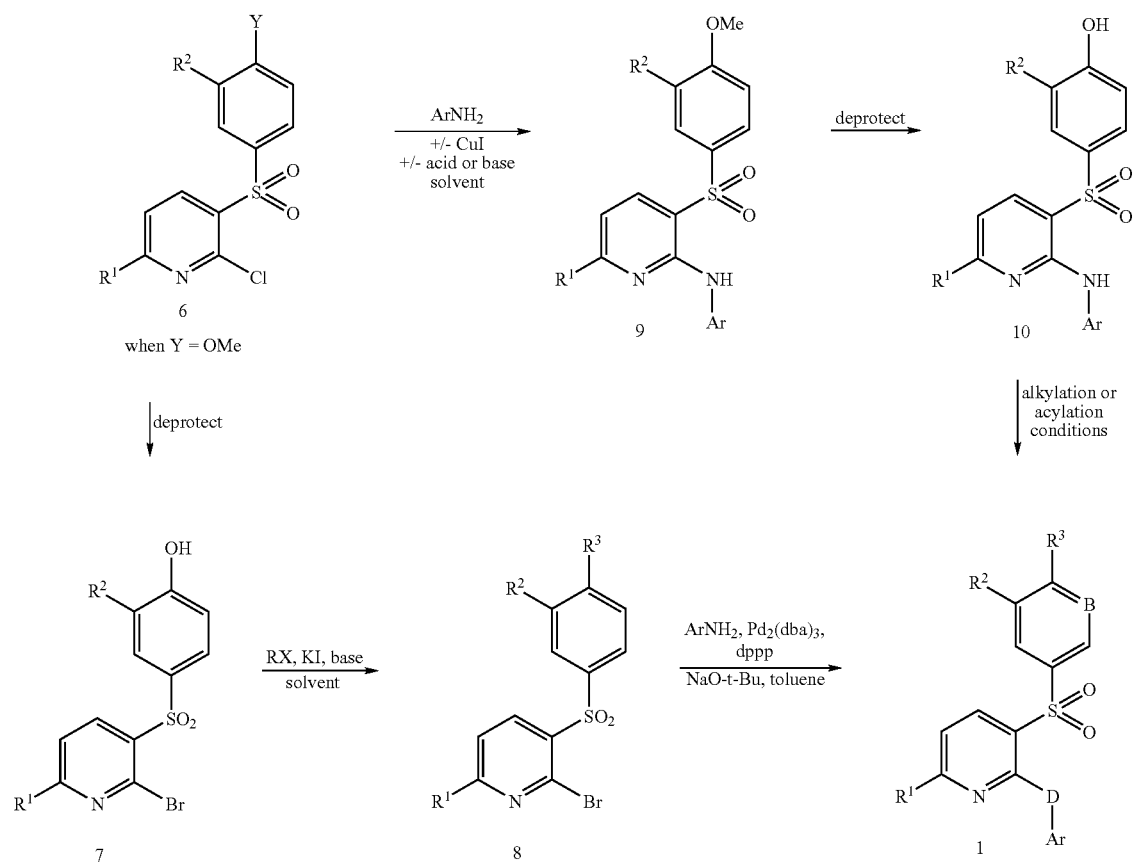

B = CH
D = NH

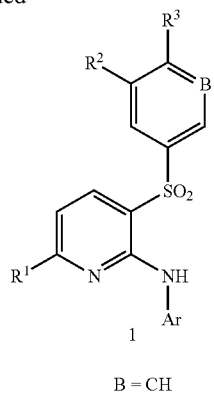

1

B = CH

Compounds of formula 1 where B=CH and D=CH$_2$ may be prepared as shown in Scheme 4. Compounds of formula 6 where B=CH and Y=F or OMe may be hydrogenated using conditions known to one skilled in the art of organic synthesis. Compounds 6 can be placed under a hydrogen atomsphere at pressures ranging from atmospheric pressure to 50 psi in the presence of a metal catalyst such as palladium on carbon (preferably 10% palladium on carbon) in a polar organic solvent such as, but not limited to, lower alkyl alcohols (C$_1$–C$_6$) (preferably ethanol or methanol). The resulting adducts 11 may be treated with a benzylic Grignard reagent. The reaction is carried out in either THF or a dialkyl ether (preferably diethyl ether) or a combination thereof at temperatures ranging from −78° C. to 35° C. The Grignard reagent may be commercially available or may need to be prepared. If the Grignard reagent needs to be prepared, it can be prepared from the corresponding benzylic halide (preferably chloride or bromide) by stirring the substrate in diethyl ether in the presence of fresh magnesium turnings using standard literature procedures. Compounds of formula 12 can be oxidized using an oxidizing agent such as, but not limited to, TPAP/NMO in a solvent such as methylene chloride to form adducts 13.

If Y=OMe, adducts 13 can be converted to adducts 1, where B=CH$_2$ and D=CH$_2$ using a two step procedure whereby deprotection of the methoxy group can be effected upon treatment of 13 with BBr$_3$, HBr, LiI in collidine (preferably LiI in collidine) or related reagents known to those skilled in the art of organic chemistry as described in *Protective Groups in Organic Synthesis*, (Greene, Wuts; 3$^{rd}$ ed., 1999, John Wiley & Sons, Inc.). The resulting intermediates may be alkylated or acetylated to form compounds of formula 1 wherein R$_3$ is joined to the aryl group with an oxygen atom. For alkylation adducts, the reaction is carried out in the presence of an alkylating agent such as an alkyl halide, alkyl mesylate, alkyl tosylate or alkyl triflate in the presence of a base such as K$_2$CO$_3$, Na$_2$CO$_3$, Et$_3$N, i-Pr$_2$NEt or alkali metal alkoxides (preferably K$_2$CO$_3$) in a polar organic solvent such as acetone, acetonitrile, dimethoxyethane, dioxane, chloroform or methylene chloride (preferably acetonitrile). Optionally, the reaction can be promoted by the addition of a salt such as KI to form compounds 1. Alternatively, this alkylation reaction can be effected using conditions described by Mitsunobu (Mitsunobu, O., *Synthesis*, 1981, 1). For acylation adducts, 1 may be formed by subjection to acylating reagents, such as symmetrical anhydrides, mixed anhydrides, acid halides or esters in the presence of a base, such as, but not limited to, Et$_3$N or i-Pr$_2$NEt in the presence or absence of solvent. Alternatively, a carboxylic acid may be coupled with the intermediate phenol to form an adduct of formula 1 where R$_3$ is an ester using coupling reagents such as, but not limited to, EDC, DCC, BOP, PyBOP and pentafluorophenol in the presence of an organic solvent such as methylene chloride or DMF. If Y=F, 13 can be reacted to form 1 using the conditions illustrated in Scheme 5.

Scheme 4

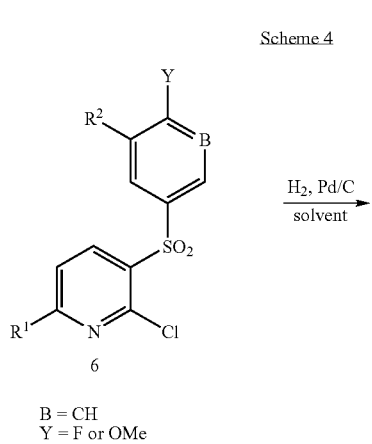

6

B = CH
Y = F or OMe

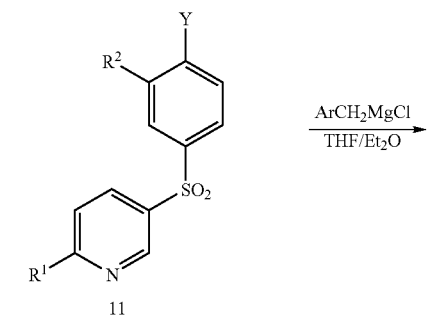

11

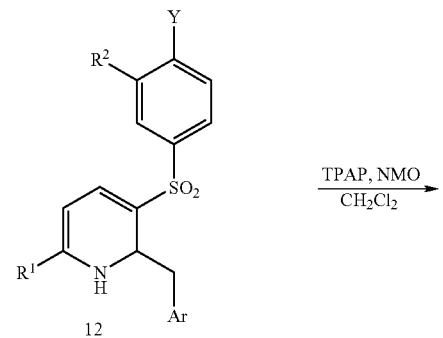

12

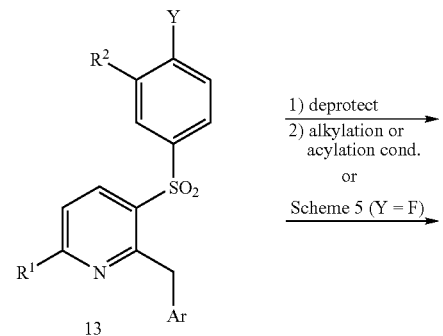

13

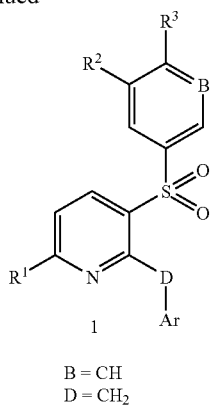

B = CH
D = CH$_2$

Compounds where R$_3$ is linked to the phenyl group with a nitrogen atom can be prepared from compounds 13 where Y=F (Scheme 5). Compounds 13 may be prepared using the appropriate reactions disclosed in Schemes 1–2. Treatment of 13 with mono or dialkylamines or arylamines (NHR$^d$R$^e$) in the presence or absence of base and in the presence or absence of solvent will provide adducts 1 where B=CH. The alkyl groups R$^d$ and R$^e$ may or may not be joined together to form a ring and may or may not contain heteroatoms. If a base is present, bases such as, but not limited to, Et$_3$N, i-Pr$_2$NEt alkali earth metal hydrides (preferably sodium hydride), bis(trialkylsilyl)amides (preferably sodium bis(trialkylsilyl)amide), lithium dialkylamides (preferably lithium diisopropyl amide) or alkyl-lithiums can be used. If the reaction is carried out in the presence of a solvent, solvents such as THF, dimethoxyethane, dioxane or DMF are used (preferably dioxane). The reaction is carried out at temperatures ranging from 22° C. to 150° C. If the temperature of the reaction mixture exceeds the boiling point of the solvent, the reaction must be carried out in a pressure vessel.

Scheme 5

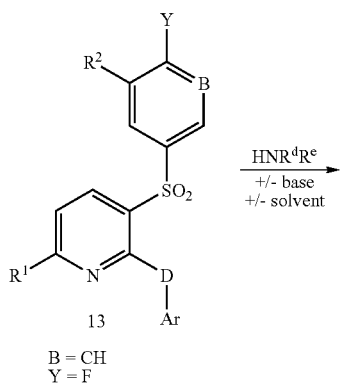

B = CH
Y = F

B = CH

Phenols of formula 10, which may be prepared by the route outlined in Scheme 2, are treated with trifluoromethanesulfonyl chloride in the presence of bases such as Et$_3$N, i-Pr$_2$NEt, collidine or 2,6-dimethylpyridine in a non-protic organic solvent (preferably dichloromethane) to generate the corresponding triflates 14 (Scheme 6). Compounds of formula 1 may be prepared from 14, wherein R$_3$ is linked to the phenyl group with a carbon atom, by reaction of 14 with an alkyl metal species (metals may include, but are not limited to, boron, tin, zinc, magnesium, and silicon) in the presence or absence of a metal catalyst (preferably PdL$_{2-4}$ where L is a ligand such as, but not limited to, PPh$_3$, Cl, OAc, or dba or a combination thereof) in an aprotic organic solvent such as, but not limited to, CH$_2$Cl$_2$, CHCl$_3$, DME, DMF, toluene or dioxane at temperatures ranging from 22° C. to 180° C. In addition, the reaction may also be carried out in the presence of a base, such as, but not limited to, Na$_2$CO$_3$, K$_2$CO$_3$, Et$_3$N or i-Pr$_2$NEt, (preferably Na$_2$CO$_3$ or Et$_3$N) and in the presence or absence of an inorganic salt (preferably LiCl). In addition, it may be necessary to add a phosphine based ligand (PR$^f_3$, R$^f$=C$_1$–C$_6$ alkyl or phenyl) to the reaction mixture. The conditions described above are known to one skilled in the art of organic synthesis as Stille, Suzuki or Negishi couplings.

Scheme 6

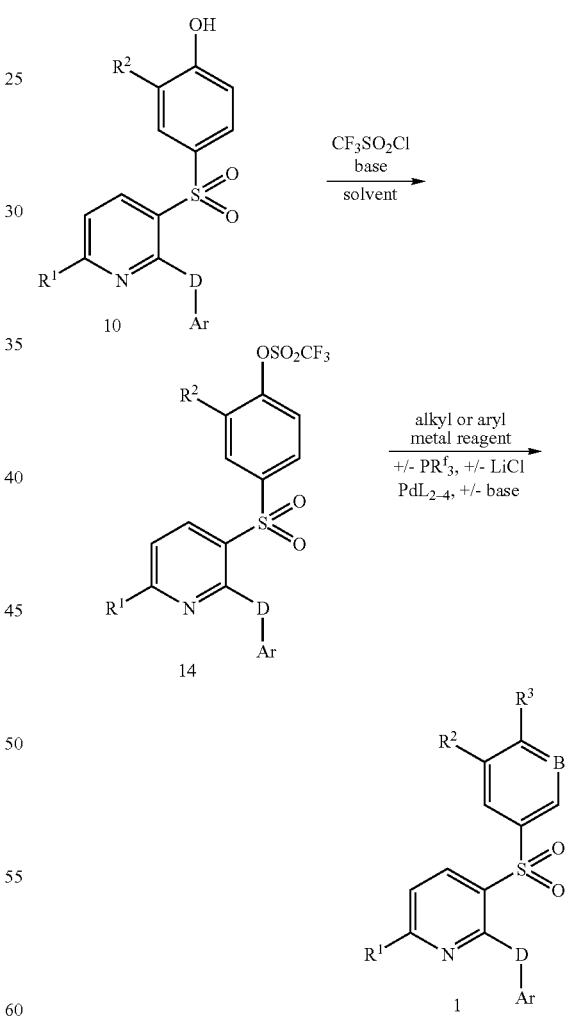

B = CH

Compounds of formula 1 where B=N may be prepared as outlined in Scheme 7. Compounds 17 may be prepared as illustrated in Scheme 1. Treatment of 17 with alcohols $R^dOH$ ($R^d$=alkyl or aryl) or mono or dialkylamines or arylamines ($NHR^dR^e$) in the presence or absence of base and in the presence or absence of solvent furnishes adducts 18. The alkyl groups $R^d$ and $R^e$ may or may not be joined together to form a ring and may or may not contain heteroatoms. If a base is present, bases such as, but not limited to, $Et_3N$, i-$Pr_2NEt$ alkali earth metal hydrides (preferably sodium hydride), bis(trialkylsilyl)amides (preferably sodium bis(trialkylsilyl)amide), lithium dialkylamides (preferably lithium diisopropyl amide) or alkyl-lithiums can be used. If the reaction is carried out in the presence of a solvent, solvents such as THF, dimethoxyethane, dioxane or DMF are used (preferably dioxane). The reaction is carried out at temperatures ranging from 22° C. to 150° C. If the temperature of the reaction mixture exceeds the boiling point of the solvent, the reaction must be carried out in a pressure vessel. Compounds of formula 18 can be prepared from 17, wherein $R_3$ is linked to the phenyl group with a carbon atom, by reaction of 17 with an alkyl metal species (metals may include, but are not limited to, boron, tin, zinc, magnesium, and silicon) in the presence or absence of a metal catalyst (preferably $PdL_{2-4}$ where L is a ligand such as, but not limited to, $PPh_3$, Cl, OAc, or dba or a combination thereof) in an aprotic organic solvent such as, but not limited to, $CH_2Cl_2$, $CHCl_3$, DME, DMF, toluene or dioxane at temperatures ranging from 22° C. to 180° C. In addition, the reaction may also be carried out in the presence of a base, such as, but not limited to, $Na_2CO_3$, $K_2CO_3$, $Et_3N$ or i-$Pr_2NEt$, (preferably $Na_2CO_3$ or $Et_3N$) and in the presence or absence of an inorganic salt (preferably LiCl). In addition, it may be necessary to add a phosphine based ligand ($PR^f_3$, $R^f=C_1-C_6$ alkyl or phenyl) to the reaction mixture. The conditions described above are known to one skilled in the art of organic synthesis as Stille (Stille, J. K., *Angew, Chem., Int. Ed. Engl.*, 1986, 25, 508–524), Suzuki (Suzuki, A., *Pure and Appl. Chem.*, 1985, 57, 1749–1758), Negishi (Negishi, E., *Acc. Chem. Res.*, 1982, 15, 240–348) or Kumada (Tamao, K.; Sumitani, K.; Kiso, Y.; Zembayashi, M.; Fujioka, A.; Kodma, S.-i.; Nakajima, I.; Minato, A.; Kumada, M., *Bull. Chem. Soc. Jpn.*, 1976, 49, 1958–1969) couplings. Alternatively, in place of a coupling reaction, a carbon nucleophile, such as NaCN, may be reacted with 17 to form compounds of formula 18.

Compounds of formula 1 where B=N and D=NH may be formed from adducts 18 by treatment of 18 with an aniline in the presence or absence of either acid or base and in the presence or absence of solvent at temperatures ranging from 22° C. to 210° C. If the reaction is carried out in the presence of a base, bases such as $Et_3N$, i-$Pr_2NEt$, $K_2CO_3$ or $Na_2CO_3$ are used. If the reaction is carried out in the presence of acid, acids such as organic acids are used (preferably p-TsOH). If the reaction is carried out in the presence of a solvent, an organic solvent such as an alcohol or ethylene glycol is used. Compounds of formula 1 where B=N and D=$CH_2$ may be formed from adducts 18 by employing the reactions described in steps 1–3 of Scheme 4.

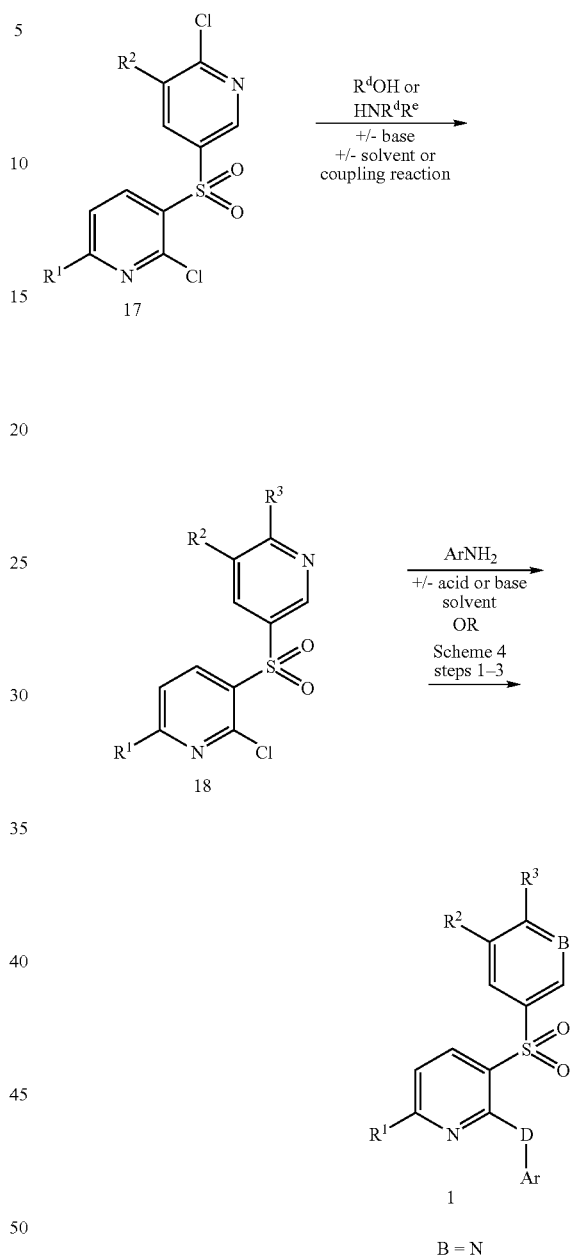

Compounds of formula 1 where $R_2$ is a substituent other than H or $R_2$ and $R_3$ are both substituents other than H can be prepared using the routes in Schemes 1–7 by starting with the appropriate starting materials.

Various analogs that may be synthesized using Schemes 1–7 are listed in Table 1. Compounds having a designation of a, b, c or d were tested in the CRF assays described below and exhibited the following levels of activity: a, $K_i \leq 100$ nM; b, 100 nM<$K_i \leq 500$ nM, c, 500 nM<$K_i \leq 5,000$ nM, d—activity reported in percent inhibition at 10 µM. Compounds not having such a designation are prophetic examples.

TABLE 1

[Structure: pyridine bearing R1, SO2-aryl(B) with R2, R3, and D-Ar substituent]

| Ex | B | D | R₁ | R₂ | R₃ | Ar | Mp (° C.) | activity |
|---|---|---|---|---|---|---|---|---|
| 1 | CH | NH | Me | H | 2-OMe—OBn | 2-Me-4-OMe—Ph | 70–72 | d |
| 2 | CH | NH | Me | H | 2-OMe—OBn | 2-Cl-4-OMe-5-F—Ph | 62–64 | d |
| 3 | CH | NH | Me | H | 2-OMe—OBn | 2-Cl-4-NMe₂-5-F—Ph | 68–70 | d |
| 4 | CH | NH | Me | H | 2-OMe—OBn | 2-Me-4,5-OMe₂—Ph | 62–66 | d |
| 5 | CH | NH | Me | H | 2-OMe—OBn | 2-Cl-4-OCHF₂—Ph | 124–125 | d |
| 6 | CH | NH | Me | H | 2-OMe—OBn | 2-Cl-4,5-OMe₂—Ph | 149–151 | d |
| 7 | CH | NH | Me | H | 2-OMe—OBn | 2-Cl-4-SO₂Me—Ph | 100–102 | d |
| 8 | CH | NH | Me | H | 2-OMe—OBn | 2-CN-4-Cl—Ph | 178–180 | d |
| 9 | CH | NH | Me | H | OMe | 2,4,6-Me₃—Ph | 165–167 | b |
| 10 | CH | NH | Me | H | OH | 2,4,6-Me₃—Ph | 226–228 | c |
| 11 | CH | NH | Me | H | OBn | 2,4,6-Me₃—Ph | 158–160 | a |
| 12 | CH | NH | Me | H | OEt | 2,4,6-Me₃—Ph | 157–159 | d |
| 13 | CH | NH | Me | H | Oallyl | 2,4,6-Me₃—Ph | 138–140 | b |
| 14 | CH | NH | Me | H | OC₃H₆CN | 2,4,6-Me₃—Ph | 160–162 | c |
| 15 | CH | NH | Me | H | OC₄H₈CN | 2,4,6-Me₃—Ph | 115–116 | b |
| 16 | CH | NH | Me | H | OC₃H₆OH | 2,4,6-Me₃—Ph | 152–153 | c |
| 17 | CH | NH | Me | H | OCH₂CO₂Et | 2,4,6-Me₃—Ph | 116–118 | c |
| 18 | CH | NH | Me | H | OEtCHCO₂Et | 2,4,6-Me₃—Ph | 111–113 | b |
| 19 | CH | NH | Me | H | OCH₂(2-pyridyl) | 2,4,6-Me₃—Ph | 182–184 | b |
| 20 | CH | NH | Me | H | OCH₂(3,5-Cl₂-4-pyridyl) | 2,4,6-Me₃—Ph | 192–201 | b |
| 21 | CH | NH | Me | H | OCH₂(2-Me-4-thiazolyl) | 2,4,6-Me₃—Ph | 200–201 | b |
| 22 | CH | NH | Me | H | 4-F-OBn | 2,4,6-Me₃—Ph | 178–180 | b |
| 23 | CH | NH | Me | H | 4-CN-OBn | 2,4,6-Me₃—Ph | 208–210 | b |
| 24 | CH | NH | Me | H | 3-CN-OBn | 2,4,6-Me₃—Ph | 155–158 | a |
| 25 | CH | NH | Me | H | 3-CO₂Me—OBn | 2,4,6-Me₃—Ph | 148–150 | a |
| 26 | CH | NH | Me | H | 3-OMe—OBn | 2,4,6-Me₃—Ph | 124–126 | a |
| 27 | CH | NH | Me | H | 2-OMe—OBn | 2,4,6-Me₃—Ph | 148–150 | a |
| 28 | CH | NH | Me | H | 2-CN—OBn | 2,4,6-Me₃—Ph | 208–210 | a |
| 29 | CH | NH | Me | H | 2-NO₂—OBn | 2,4,6-Me₃—Ph | 153–155 | a |
| 30 | CH | NH | Me | H | 3,5-OMe₂—OBn | 2,4,6-Me₃—Ph | 107–109 | a |
| 31 | CH | NH | Me | H | 2,5-OMe₂—OBn | 2,4,6-Me₃—Ph | 128–130 | a |
| 32 | CH | NH | Me | H | 2,3-OMe₂—OBn | 2,4,6-Me₃—Ph | 124–126 | a |
| 33 | CH | NH | Me | H | 2,3-F₂—OBn | 2,4,6-Me₃—Ph | 136–138 | a |
| 34 | CH | NH | Me | H | 2-F-6-NO₂—OBn | 2,4,6-Me₃—Ph | 132–134 | a |
| 35 | CH | NH | Me | H | 3-Ac-6-OMe—OBn | 2,4,6-Me₃—Ph | 141–143 | b |
| 36 | CH | NH | Me | H | 2,6-Me₂—OBn | 2,4,6-Me₃—Ph | 136–138 | a |
| 37 | CH | NH | Me | Cl | F | 2,4,6-Me₃—Ph | 139–141 | b |
| 38 | CH | NH | Me | Me | Me | 2,4,6-Me₃—Ph | oil | b |
| 39 | CH | NH | Me | OMe | OMe | 2,4,6-Me₃—Ph | amorph | c |
| 40 | CH | NH | Me | Cl | Cl | 2,4,6-Me₃—Ph | amorph | b |
| 41 | CH | NH | Me | H | Me | 2,4,6-Me₃—Ph | oil | b |
| 42 | CH | NH | Me | H | Et | 2,4,6-Me₃—Ph | amorph | a |
| 43 | CH | NH | Me | H | isopropyl | 2,4,6-Me₃—Ph | amorph | b |
| 44 | CH | NH | Me | H | OCF₃ | 2,4,6-Me₃—Ph | amorph | b |
| 45 | CH | NH | Me | H | F | 2,4,6-Me₃—Ph | amorph | b |
| 46 | CH | NH | Me | H | Br | 2,4,6-Me₃—Ph | 140–141 | a |
| 47 | CH | NH | Me | H | ethyne | 2,4,6-Me₃—Ph | amorph | a |
| 48 | CH | NH | Me | H | Ph | 2,4,6-Me₃—Ph | 193–195 | a |
| 49 | CH | NH | Me | H | 2-OMePh | 2,4,6-Me₃—Ph | amorph | a |
| 50 | CH | NH | Me | H | CH₂OH | 2,4,6-Me₃—Ph | amorph | b |
| 51 | CH | NH | Me | H | CH₂N-mesityl | 2,4,6-Me₃—Ph | — | c |
| 52 | CH | NH | Me | H | CHO | 2,4,6-Me₃—Ph | amorph | c |
| 53 | CH | NH | Me | H | CH(OH)Ph | 2,4,6-Me₃—Ph | amorph | b |
| 54 | CH | NH | Me | H | COPh | 2,4,6-Me₃—Ph | 222–225 | a |
| 55 | CH | NH | Me | H | CH₂OAc | 2,4,6-Me₃—Ph | 132–134 | b |
| 56 | CH | NH | Me | OMe | H | 2,4,6-Me₃—Ph | 87–88 | b |
| 57 | CH | NH | Me | OH | H | 2,4,6-Me₃—Ph | 196–197 | b |
| 58 | CH | NH | Me | OEt | H | 2,4,6-Me₃—Ph | 96–97 | b |

TABLE 1-continued

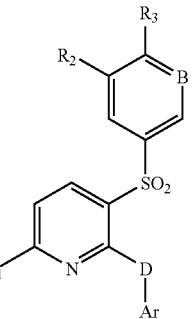

| Ex | B | D | R₁ | R₂ | R₃ | Ar | Mp (° C.) | activity |
|---|---|---|---|---|---|---|---|---|
| 59 | CH | NH | Me | Oallyl | H | 2,4,6-Me₃—Ph | amorph | b |
| 60 | CH | NH | Me | OBn | H | 2,4,6-Me₃—Ph | amorph | b |
| 61 | CH | NH | Me | 4-F—OBn | H | 2,4,6-Me₃—Ph | amorph | b |
| 62 | CH | NH | Me | 3-OMe—OBn | H | 2,4,6-Me₃—Ph | amorph | b |
| 63 | CH | NH | Me | 3,5-OMe₂—OBn | H | 2,4,6-Me₃—Ph | 120–121 | b |
| 64 | CH | NH | Me | OCH₂(4-Cl-3-pyridyl) | H | 2,4,6-Me₃—Ph | amorph | b |
| 65 | CH | NH | Me | OCH₂(3,5-Cl₂-4-pyridyl) | H | 2,4,6-Me₃—Ph | amorph | b |
| 66 | CH | NH | Me | H | Et | 2,4-Me₂—Ph | oil | b |
| 67 | CH | NH | Me | H | Et | 2-Me-4-OMe—Ph | oil | a |
| 68 | CH | NH | Me | H | Et | 2,4-(OMe)₂—Ph |  | b |
| 69 | CH | NH | Me | H | Et | 2-Cl-4-OMe—Ph | 110–112 | b |
| 70 | CH | NH | Me | H | Et | 2,4,5-Me₃—Ph |  | a |
| 101 | CH | CH₂ | Me | H | 2-OMe—OBn | 2-Me-4-OMe—Ph |  |  |
| 102 | CH | CH₂ | Me | H | 2-OMe—OBn | 2-Cl-4-OMe-5-F—Ph |  |  |
| 103 | CH | CH₂ | Me | H | 2-OMe—OBn | 2-Cl-4-NMe₂-5-F—Ph |  |  |
| 104 | CH | CH₂ | Me | H | 2-OMe—OBn | 2-Me-4,5-OMe₂—Ph |  |  |
| 105 | CH | CH₂ | Me | H | 2-OMe—OBn | 2-Cl-4-OCHF₂—Ph |  |  |
| 106 | CH | CH₂ | Me | H | 2-OMe—OBn | 2-Cl-4,5-OMe₂—Ph |  |  |
| 107 | CH | CH₂ | Me | H | 2-OMe—OBn | 2-Cl-4-SO₂Me—Ph |  |  |
| 108 | CH | CH₂ | Me | H | 2-OMe—OBn | 2-CN-4-Cl—Ph |  |  |
| 109 | CH | CH₂ | Me | H | Et | 2-Cl-4-OMe—Ph |  |  |
| 110 | CH | CH₂ | Me | H | OH | 2,4,6-Me₃—Ph |  |  |
| 111 | CH | CH₂ | Me | H | Et | 2,4,5-Me₃—Ph |  |  |
| 112 | CH | CH₂ | Me | H | OEt | 2,4,6-Me₃—Ph |  |  |
| 113 | CH | CH₂ | Me | H | Oallyl | 2,4,6-Me₃—Ph |  |  |
| 114 | CH | CH₂ | Me | H | OC₃H₆CN | 2,4,6-Me₃—Ph |  |  |
| 115 | CH | CH₂ | Me | H | OC₄H₈CN | 2,4,6-Me₃—Ph |  |  |
| 116 | CH | CH₂ | Me | H | OC₃H₆OH | 2,4,6-Me₃—Ph |  |  |
| 117 | CH | CH₂ | Me | H | OCH₂CO₂Et | 2,4,6-Me₃—Ph |  |  |
| 118 | CH | CH₂ | Me | H | OEtCHCO₂Et | 2,4,6-Me₃—Ph |  |  |
| 119 | CH | CH₂ | Me | H | OCH₂(2-pyridyl) | 2,4,6-Me₃—Ph |  |  |
| 120 | CH | CH₂ | Me | H | OCH₂(3,5-Cl₂-4-pyridyl) | 2,4,6-Me₃—Ph |  |  |
| 121 | CH | CH₂ | Me | H | OCH₂(2-Me-4-thiazolyl) | 2,4,6-Me₃—Ph |  |  |
| 122 | CH | CH₂ | Me | H | 4-F—OBn | 2,4,6-Me₃—Ph |  |  |
| 123 | CH | CH₂ | Me | H | 4-CN—OBn | 2,4,6-Me₃—Ph |  |  |
| 124 | CH | CH₂ | Me | H | 3-CN—OBn | 2,4,6-Me₃—Ph |  |  |
| 125 | CH | CH₂ | Me | H | 3-CO₂Me—OBn | 2,4,6-Me₃—Ph |  |  |
| 126 | CH | CH₂ | Me | H | 3-OMe—OBn | 2,4,6-Me₃—Ph |  |  |
| 127 | CH | CH₂ | Me | H | 2-OMe—OBn | 2,4,6-Me₃—Ph |  |  |
| 128 | CH | CH₂ | Me | H | 2-CN—OBn | 2,4,6-Me₃—Ph |  |  |
| 129 | CH | CH₂ | Me | H | 2-NO₂—OBn | 2,4,6-Me₃—Ph |  |  |
| 130 | CH | CH₂ | Me | H | 3,5-OMe₂—OBn | 2,4,6-Me₃—Ph |  |  |
| 131 | CH | CH₂ | Me | H | 2,5-OMe₂—OBn | 2,4,6-Me₃—Ph |  |  |
| 132 | CH | CH₂ | Me | H | 2,3-OMe₂—OBn | 2,4,6-Me₃—Ph |  |  |
| 133 | CH | CH₂ | Me | H | 2,3-F₂—OBn | 2,4,6-Me₃—Ph |  |  |
| 134 | CH | CH₂ | Me | H | 2-F-6-NO₂—OBn | 2,4,6-Me₃—Ph |  |  |
| 135 | CH | CH₂ | Me | H | 3-Ac-6-OMe—OBn | 2,4,6-Me₃—Ph |  |  |
| 136 | CH | CH₂ | Me | H | 2,6-Me₂—OBn | 2,4,6-Me₃—Ph |  |  |
| 137 | CH | CH₂ | Me | Cl | F | 2,4,6-Me₃—Ph |  |  |
| 138 | CH | CH₂ | Me | Me | Me | 2,4,6-Me₃—Ph |  |  |
| 139 | CH | CH₂ | Me | OMe | OMe | 2,4,6-Me₃—Ph |  |  |
| 140 | CH | CH₂ | Me | Cl | Cl | 2,4,6-Me₃—Ph |  |  |
| 141 | CH | CH₂ | Me | H | Me | 2,4,6-Me₃—Ph |  |  |
| 142 | CH | CH₂ | Me | H | Et | 2,4,6-Me₃—Ph |  |  |

TABLE 1-continued

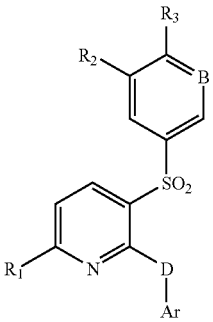

| Ex | B | D | R₁ | R₂ | R₃ | Ar | Mp (° C.) | activity |
|---|---|---|---|---|---|---|---|---|
| 143 | CH | CH₂ | Me | H | isopropyl | 2,4,6-Me₃—Ph | | |
| 144 | CH | CH₂ | Me | H | OCF₃ | 2,4,6-Me₃—Ph | | |
| 145 | CH | CH₂ | Me | H | F | 2,4,6-Me₃—Ph | | |
| 146 | CH | CH₂ | Me | H | Br | 2,4,6-Me₃—Ph | | |
| 146 | CH | CH₂ | Me | H | Br | 2,4,6-Me₃—Ph | | |
| 147 | CH | CH₂ | Me | H | ethyne | 2,4,6-Me₃—Ph | | |
| 148 | CH | CH₂ | Me | H | Ph | 2,4,6-Me₃—Ph | | |
| 149 | CH | CH₂ | Me | H | 2-OMePh | 2,4,6-Me₃—Ph | | |
| 150 | CH | CH₂ | Me | H | CH₂N-mesityl | 2,4,6-Me₃—Ph | | |
| 151 | CH | CH₂ | Me | H | CH₂OH | 2,4,6-Me₃—Ph | | |
| 152 | CH | CH₂ | Me | H | CHO | 2,4,6-Me₃—Ph | | |
| 153 | CH | CH₂ | Me | H | CH(OH)Ph | 2,4,6-Me₃—Ph | | |
| 154 | CH | CH₂ | Me | H | COPh | 2,4,6-Me₃—Ph | | |
| 155 | CH | CH₂ | Me | H | CH₂OAc | 2,4,6-Me₃—Ph | | |
| 156 | CH | CH₂ | Me | OMe | H | 2,4,6-Me₃—Ph | | |
| 157 | CH | CH₂ | Me | OH | H | 2,4,6-Me₃—Ph | | |
| 158 | CH | CH₂ | Me | OEt | H | 2,4,6-Me₃—Ph | | |
| 159 | CH | CH₂ | Me | Oallyl | H | 2,4,6-Me₃—Ph | | |
| 160 | CH | CH₂ | Me | OBn | H | 2,4,6-Me₃—Ph | | |
| 161 | CH | CH₂ | Me | 4-F—OBn | H | 2,4,6-Me₃—Ph | | |
| 162 | CH | CH₂ | Me | 3-OMe—OBn | H | 2,4,6-Me₃—Ph | | |
| 163 | CH | CH₂ | Me | 3,5-OMe₂—OBn | H | 2,4,6-Me₃—Ph | | |
| 164 | CH | CH₂ | Me | OCH₂(4-Cl-3-pyridyl) | H | 2,4,6-Me₃—Ph | | |
| 165 | CH | CH₂ | Me | OCH₂(3,5-Cl₂-4-pyridyl) | H | 2,4,6-Me₃—Ph | | |
| 166 | CH | CH₂ | Me | H | Et | 2,4-Me₂—Ph | | |
| 167 | CH | CH₂ | Me | H | Et | 2-Me-4-OMe—Ph | | |
| 168 | CH | CH₂ | Me | H | Et | 2,4-(OMe)₂—Ph | | |
| 169 | CH | NH | CN | H | 2-OMe—OBn | 2,4,6-Me₃—Ph | | |
| 170 | CH | NH | CN | H | 2-OMe—OBn | 2,4-Me₂—Ph | | |
| 171 | CH | NH | CN | H | 2-OMe—OBn | 2-Me-4-OMe—Ph | | |
| 172 | CH | NH | CN | H | 2-OMe—OBn | 2,4-(OMe)₂—Ph | | |
| 173 | CH | NH | Me | H | 2-OMe—OBn | 2,6-Cl₂-4-OCF₃—Ph | | |
| 174 | CH | NH | Me | H | 2-OMe—OBn | 2,6-Cl₂-4-CF₃—Ph | | |
| 175 | CH | NH | Me | H | 2-OMe—OBn | 2,6-Cl₂-4-CN—Ph | | |
| 176 | CH | NH | Me | H | 2-OMe—OBn | 2-Cl-4-CN-6-Me—Ph | | |
| 177 | CH | NH | Me | H | 2-OMe—OBn | 2,6-Cl₂-4-OMe—Ph | | |
| 178 | CH | NH | Me | H | 2-OMe—OBn | 2,6-Cl₂-OCHF₂—Ph | | |
| 179 | CH | NH | Me | H | 2-OMe—OBn | 2-Cl-4-OCF₃-6-Me—Ph | | |
| 180 | CH | NH | Me | H | 2-OMe—OBn | 2,4-OMe₂-3-pyridyl | | |
| 181 | CH | NH | Me | H | 2-OMe—OBn | 2,4-Me-3-pyridyl | | |
| 182 | CH | NH | Me | H | 2-OMe—OBn | 2-Me-4-OMe-3-pyridyl | | |
| 183 | CH | NH | Me | H | 2-OMe—OBn | 2,6-Me₂-4-OMe-3-pyridyl | | |
| 184 | CH | NH | Me | H | 2-OMe—OBn | 2-CF₃-4-OMe-3-pyridyl | | |
| 185 | CH | NH | Me | H | 2-OMe—OBn | 2-OMe-4-CF₃-3-pyridyl | | |
| 186 | CH | NH | Me | H | 2-OMe—OBn | 2-Me-4-CF₃-3-pyridyl | | |
| 187 | N | NH | Me | H | 2-OMe—OBn | 2,4,6-Me₃—Ph | | |
| 188 | N | NH | Me | H | 3-OMe—OBn | 2,4,6-Me₃—Ph | | |
| 189 | N | NH | Me | H | 4-OMe—OBn | 2,4,6-Me₃—Ph | | |
| 190 | N | NH | Me | H | OMe | 2,4,6-Me₃—Ph | | |
| 191 | N | NH | Me | H | OBn | 2,4,6-Me₃—Ph | | |
| 192 | N | NH | Me | H | OEt | 2,4,6-Me₃—Ph | | |
| 193 | N | NH | Me | H | Oallyl | 2,4,6-Me₃—Ph | | |
| 194 | N | NH | Me | H | 2-CN—OBn | 2,4,6-Me₃—Ph | | |
| 195 | N | NH | Me | H | 3-CN—OBn | 2,4,6-Me₃—Ph | | |

Also provided herein are pharmaceutical compositions comprising compounds of this invention and a pharmaceutically acceptable carrier, which are media generally accepted in the art for the delivery of biologically active agents to animals, in particular, mammals. Pharmaceutically acceptable carriers are formulated according to a number of factors well within the purview of those of ordinary skill in the art to determine and account for. These include, without limitation: the type and nature of the active agent being formulated; the subject to which the agent-containing composition is to be administered; the intended route of administration of the composition; and, the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, well known to those of ordinary skill in the art. Descriptions of suitable pharmaceutically acceptable carriers, and factors involved in their selection, are found in a variety of readily available sources, e.g., *Remington's Pharmaceutical Sciences*, 17$^{th}$ ed., Mack Publishing Company, Easton, Pa., 1985, the contents of which are incorporated herein by reference.

This invention thus further provides a method of treating a subject afflicted with a disorder characterized by CRF overexpression, such as those described hereinabove, which comprises administering to the subject a pharmaceutical composition provided herein. Such compositions generally comprise a therapeutically effective amount of a compound provided herein, that is, an amount effective to ameliorate, lessen or inhibit disorders characterized by CRF overexpression. Such amounts typically comprise from about 0.1 to about 1000 mg of the compound per kg of body weight of the subject to which the composition is administered. Therapeutically effective amounts can be administered according to any dosing regimen satisfactory to those of ordinary skill in the art.

Administration is, for example, by various parenteral means. Pharmaceutical compositions suitable for parenteral administration include various aqueous media such as aqueous dextrose and saline solutions; glycol solutions are also useful carriers, and preferably contain a water soluble salt of the active ingredient, suitable stabilizing agents, and if necessary, buffer substances. Antioxidizing agents, such as sodium bisulfite, sodium sulfite, or ascorbic acid, either alone or in combination, are suitable stabilizing agents; also used are citric acid and its salts, and EDTA. In addition, parenteral solutions can contain preservatives such as benzalkonium chloride, methyl- or propyl-paraben, and chlorobutanol.

Alternatively, compositions can be administered orally in solid dosage forms, such as capsules, tablets and powders; or in liquid forms such as elixirs, syrups, and/or suspensions. Gelatin capsules can be used to contain the active ingredient and a suitable carrier such as but not limited to lactose, starch, magnesium stearate, stearic acid, or cellulose derivatives. Similar diluents can be used to make compressed tablets. Both tablets and capsules can be manufactured as sustained release products to provide for continuous release of medication over a period of time. Compressed tablets can be sugar-coated or film-coated to mask any unpleasant taste, or used to protect the active ingredients from the atmosphere, or to allow selective disintegration of the tablet in the gastrointestinal tract.

This invention is described in the following examples, which those of ordinary skill in the art will readily understand are not limiting on the invention as defined in the claims which follow thereafter.

EXAMPLES

Abbreviations used in the Examples are defined as follows: "1×" for once, "2×" for twice, "3×" for thrice, "° C." for degrees Celsius, "eq" for equivalent or equivalents, "g" for gram or grams, "mg" for milligram or milligrams, "mL" for milliliter or milliliters, μL for microliters, "$^1$H" for proton, "h" for hour or hours, "M" for molar, "min" for minute or minutes, "MHz" for megahertz, "MS" for mass spectroscopy, "NMR" for nuclear magnetic resonance spectroscopy, "rt" for room temperature, "tlc" for thin layer chromatography, "v/v" for volume to volume ratio, "α", "β", "R" and "S" are stereochemical designations familiar to those skilled in the art.

Example 1

{3-[4-(2-Methoxybenzyloxy)-benzenesulfonyl]-6-methylpyridin-2-yl}-(4-methoxy-2-methylphenyl)-amine

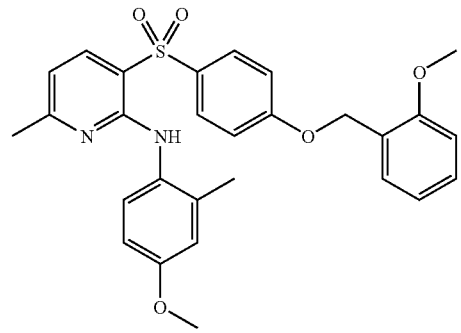

Part A. 3-Iodo-6-methyl-1H-pyridin-2-one

In a 2-liter flask 6-methyl-2-pyridone (25 g, 0.227 mol), powdered I$_2$ (72 g, 0.282 mol) and NaHCO$_3$ (25 g, 0.297 mol) were stirred in a mixture of dichloromethane (450 mL) and water (600 mL) at 25° C. for 5 days. The excess I$_2$ was quenched with a saturated solution of Na$_2$S$_2$O$_5$ (150 mL) and the organic layer was separated. The aqueous layer was extracted with dichloromethane (2×250 mL each) and the combined organic extracts were dried and stripped in vacuo. The residue was recrystallized from ethyl acetate (~1 liter) to give the first crop of product (11.77 g). The mother liquor was stripped in vacuo and the residue was recrystallized from methanol (~400 mL) to give 3.8 g of 3,5-diiodo-6-methyl-1H-pyridin-2-one. The mother liquor was stripped in vacuo and the residue was recrystallized from EtOAc (~300 mL) with addition of hexanes (200 mL) after most of the product was crystallized to give an additional 9.85 g of 3-iodo-6-methyl-1H-pyridin-2-one. Combined yield: 21.62 g of ≧94% purity, which was carried over to the next reaction.

Part B. 3-(4-Methoxyphenylsulfanyl)-6-methyl-1H-pyridin-2-one

4-Methoxythiophenol (1.7 mL, 13.85 mmol) was added to a suspension of NaH 60% in oil (831 mg, 20.80 mmol) in DMF (30 mL) at 0° C., and the mixture was allowed to warm to 25° C. 3-Iodo-6-methyl-1H-pyridin-2-one (3 g, 12.78 mmol) was added to the solution at 0° C., followed by CuI (533 mg, 2.8 mmol). The reaction was stirred at 25° C. for 1 h and heated at 120° C. for 5 h. It was then allowed to cool and partitioned between $CH_2Cl_2$ (30 mL) and 9:1 $NH_4Cl/NH_4OH$ (30 mL) and stirred for 15 min. The mixture was extracted with $CH_2Cl_2$ (3×70 mL each) and the combined $CH_2Cl_2$ extracts were washed with water (3×30 mL), brine, dried and stripped in vacuo to give the crude product (3.6 g), which was further purified by washing with ether to give 2.93 g of 3-(4-methoxyphenylsulfanyl)-6-methyl-1H-pyridin-2-one which was used in the next step.

Part C. 2-Chloro-3-(4-methoxyphenylsulfanyl)-6-methylpyridine

The product from part B was heated at reflux in $POCl_3$ (15 mL) for 22 h. The reaction was poured into ice/water (160 mL), and after all the $POCl_3$ had been quenched it was neutralized with $Na_2CO_3$ and extracted with EtOAc (3×100 mL each). The combined organic extracts were dried and stripped in vacuo. The residue was chromatographed on silica gel (20% EtOAc/hexanes eluent) to give 2-chloro-3-(4-methoxyphenylsulfanyl)-6-methylpyridine (2.16 g).

Part D. 2-Chloro-3-(4-methoxybenzenesulfonyl)-6-methylpyridine

2-Chloro-3-(4-methoxyphenylsulfanyl)-6-methylpyridine (1.0 g, 3.76 mmol) was dissolved in $CH_2Cl_2$ (40 mL) and cooled to 0° C. m-Chloroperbenzoic acid ~77% max. (1.71 g 7.64 mmol) was added to the solution at 0° C. and the mixture was stirred at 0° C. for 1 h and at 25° C. for 20 h. The reaction was quenched with sat $Na_2S_2O_5$ (10 mL), sat $NaHCO_3$ was added (20 mL) and the mixture was extracted with $CH_2Cl_2$ (40 mL). The combined organic extracts were washed with $NaHCO_3$ (20 mL), dried and stripped in vacuo to give 1.14 g of 2-chloro-3-(4-methoxybenzenesulfonyl)-6-methylpyridine, which was used in the next step without purification.

Part E. 4-(2-Bromo-6-methylpyridine-3-sulfonyl)-phenol

2-Chloro-3-(4-methoxybenzenesulfonyl)-6-methylpyridine (4.74 g, 15.92 mmol) was suspended in HBr (84 mL, 48%). The orange reaction mixture was heated at 110° C. for 24 h. The reaction mixture was cooled to rt, diluted with $H_2O$, and was treated with $Na_2CO_3$ until neutral. The aqueous layer was extracted with EtOAc (3×). The combined organic layers were washed with brine, dried over $MgSO_4$, filtered, and concentrated to afford a colorless solid (3.22 g, 62% yield) which was used without further purification: mp 99–102° C.; $^1$H NMR (300 MHz, $CDCl_3$) δ 8.52 (d, J=7.7 Hz, 1H), 7.86 (d, J=8.8 Hz, 2H), 7.35 (d, J=8.0 Hz, 1H), 6.95 (d, J=9.1 Hz, 2H), 2.63 (s, 3H); LRMS (APCI) m/z 328.0 [(M+H)$^+$, calcd for $C_{12}H_{11}NO_3BrS$, 328.0].

Part F. 2-Bromo-3-[4-(2-methoxybenzyloxy)-benzenesulfonyl]-6-methylpyridine 4-(2-Bromo-6-methylpyridine-3-sulfonyl)-phenol from part E (3.22 g, 9.81 mmol), KI (1.95 g, 11.77 mmol), $K_2CO_3$ (1.63 g, 11.77 mmol), and 2-methoxybenzyl chloride (1.64 mL, 11.77 mmol) were suspended in MeCN (10 mL) and heated at reflux overnight. The mixture was cooled to rt, diluted with EtOAc, and filtered through a pad of Celite. The filtrate was concentrated and purified by column chromatography on silica gel (20% ethyl acetate in hexanes). Tritration with methanol afforded the desired product (3.44 g, 78% yield) as a colorless solid: mp 76–78° C.; $^1$H NMR (300 MHz, $CDCl_3$) δ 8.43 (d, J=7.6 Hz, 1H), 7.82 (d, J=7.0 Hz, 2H), 7.31 (d, J=7.0 Hz, 1H), 7.25 (d, J=8.0 Hz, 2H), 7.01 (d, J=7.0, Hz, 2H), 6.92 (d, J=6.6 Hz, 1H), 6.85 (d, J=8.0 Hz, 1H), 5.10 (s, 2H), 3.80 (s, 3H), 2.53 (s, 3H); LRMS (APCI) m/z 448.0 [(M+H)$^+$, calcd for $C_{20}H_{19}NO_4BrS$, 448.0].

Part G. {3-[4-(2-Methoxybenzyloxy)-benzenesulfonyl]-6-methylpyridin-2-yl}-(4-methoxy-2-methylphenyl)-amine 2-Bromo-3-[4-(2-methoxybenzyloxy)-benzenesulfonyl]-6-methylpyridine from part F (75 mg, 0.167 mmol), 2-methyl-4-methoxyaniline (26 μL, 0.200 mmol), Pd(dba)$_3$ (3 mg, 0.0033 mmol), dppp (3 mg, 0.0067 mmol), and NaOt-Bu (22 mg, 0.234 mmol) were suspended in toluene in a tightly capped conical vial. The reaction mixture was heated at 70° C. for 4.5 h. The mixture was cooled to rt, and diluted with ether. The organic layer was washed with brine (2×), dried over $MgSO_4$, filtered, and concentrated. Purified by preparative TLC (1000 μM silica gel plate, 15% ethyl acetate in hexanes) to furnish the desired product (13 mg, 15% yield) as a pale yellow solid: mp 70–72° C.; $^1$H NMR (300 MHz, $CDCl_3$) δ 8.31 (s, 1H), 7.93 (d, J=8.0 Hz, 1H), 7.77 (d, J=9.2 Hz, 2H), 7.52 (d, J=8.4 Hz, 1H), 7.30–7.22 (m, 2H), 6.96 (d, J=8.8 Hz, 2H), 6.90 (d, J=7.6 Hz, 1H), 6.84 (d, J=8.0 Hz, 1H), 6.68 (d, J=9.1 Hz, 2H), 6.53 (d, J=8.0 Hz, 1H), 5.23 (s, 2H), 3.78 (s, 3H), 3.73 (s, 3H), 2.27 (s, 3H), 2.10 (s, 3H); HRMS (ESI) m/z 505.1807 [(M+H)$^+$, calcd for $C_{28}H_{29}N_2O_5S$, 505.1797].

Example 2

(2-Chloro-5-fluoro-4-methoxyphenyl)-{3-[4-(2-methoxybenzyloxy)-benzenesulfonyl]-6-methylpyridin-2-yl}-amine

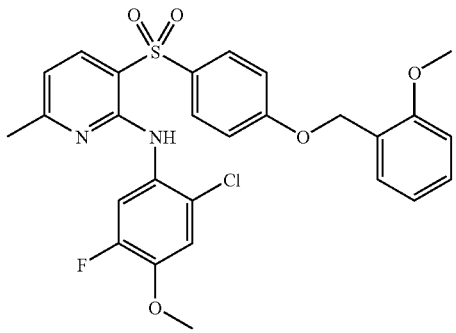

Prepared by the method described in Example 1 using the appropriate starting materials to give the desired product as a colorless solid; mp 62–64° C.; HRMS (ESI) m/z 543.1168 [(M+H)$^+$, calcd for $C_{27}H_{25}N_2O_5SFCl$, 543.1157].

Example 3

2-Chloro-5-fluoro-$N^1$-{3-[4-(2-methoxybenzyloxy)-benzenesulfonyl]-6-methylpyridin-2-yl}-$N^4,N^4$-dimethylbenzene-1,4-diamine

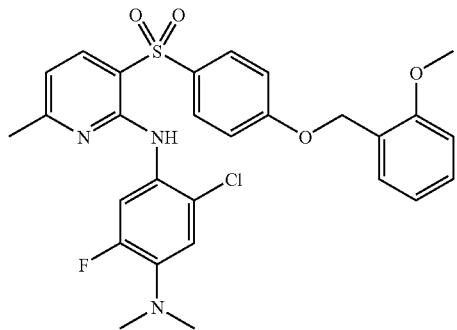

Prepared by the method described in Example 1 using the appropriate starting materials to give the desired product as a colorless solid; mp 68–70° C.; HRMS (ESI) m/z 556.1497 [(M+H)$^+$, calcd for $C_{28}H_{28}N_3O_4SFCl$, 556.1473].

Example 4

(4,5-Dimethoxy-2-methylphenyl)-{3-[4-(2-methoxybenzyloxy)-benzenesulfonyl]-6-methylpyridin-2-yl}-amine

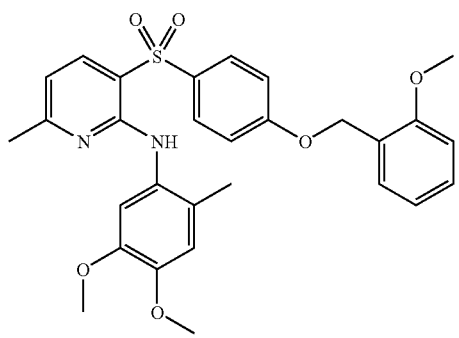

Prepared by the method described in Example 1 using the appropriate starting materials to give the desired product as a colorless solid; mp 62–66° C.; HRMS (ESI) m/z 535.1917 [(M+H)$^+$, calcd for $C_{29}H_{31}N_2O_6S$, 535.1903].

Example 5

(2-Chloro-4-difluoromethoxyphenyl)-{3-[4-(2-methoxybenzyloxy)-benzenesulfonyl]-6-methylpyridin-2-yl}-amine

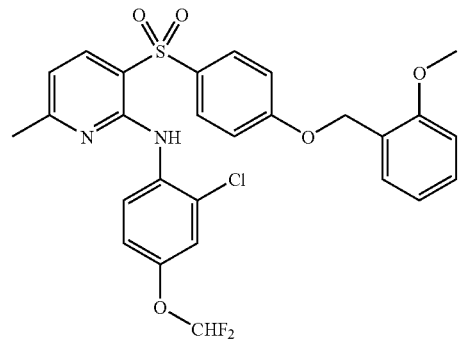

Prepared by the method described in Example 1 using the appropriate starting materials to give the desired product as a colorless solid; mp 124–125° C.; HRMS (ESI) m/z 561.1058 [(M+H)$^+$, calcd for $C_{27}H_{24}N_2O_5SF_2Cl$, 561.1063].

Example 6

(2-Chloro-4,5-dimethoxyphenyl)-{3-[4-(2-methoxybenzyloxy)-benzenesulfonyl]-6-methylpyridin-2-yl}-amine Prepared by the method described in Example 1 using the appropriate starting materials to give the desired product as a colorless solid; mp 149–151° C.; HRMS (ESI) m/z 555.1365 [(M+H)$^+$, calcd for $C_{28}H_{28}N_2O_6SCl$, 555.1357].

Example 7

(2-Chloro-4-methanesulfonylphenyl)-{3-[4-(2-methoxybenzyloxy)-benzenesulfonyl]-6-methylpyridin-2-yl}-amine

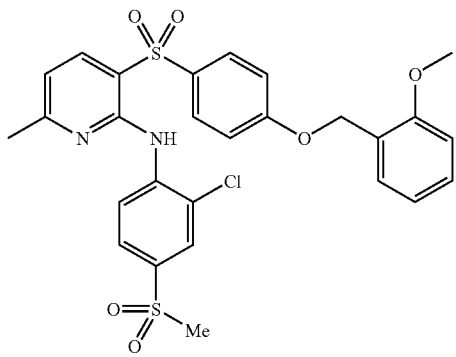

Prepared by the method described in Example 1 using the appropriate starting materials to give the desired product as a colorless solid; mp 100–102° C.; LRMS (APCI) m/z 573.0 [(M+H)+, calcd for $C_{27}H_{26}N_2O_6S_2Cl$, 573.1].

Example 8

5-Chloro-2-{3-[4-(2-methoxybenzyloxy)-benzenesulfonyl]-6-methylpyridin-2-ylamino}-benzonitrile

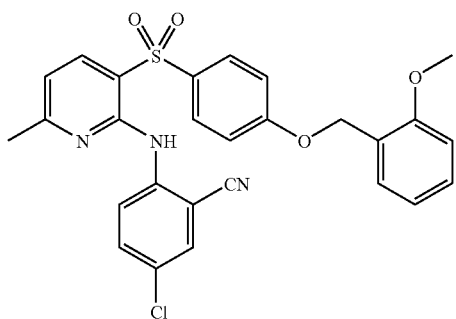

Prepared by the method described in Example 1 using the appropriate starting materials to give the desired product as a colorless solid; mp 178–180° C.; HRMS (ESI) m/z 520.1097 [(M+H)+, calcd for $C_{27}H_{23}N_3O_4SCl$, 520.1098].

Example 9

[3-(4-Methoxybenzenesulfonyl)-6-methylpyridin-2-yl]-(2,4,6-trimethylphenyl)-amine

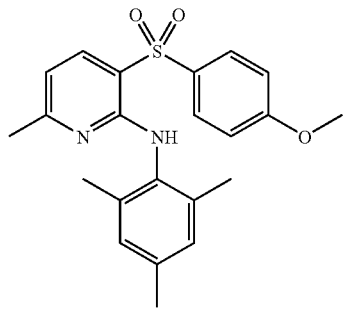

Part A. 3-Iodo-6-methyl-1H-pyridin-2-one

In a 2-liter flask 6-methyl-2-pyridone (25 g, 0.227 mol), powdered $I_2$ (72 g, 0.282 mol) and $NaHCO_3$ (25 g, 0.297 mol) were stirred in a mixture of dichloromethane (450 mL) and water (600 mL) at 25° C. for 5 days. The excess $I_2$ was quenched with a saturated solution of $Na_2S_2O_5$ (150 mL) and the organic layer was separated. The aqueous layer was extracted with dichloromethane (2×250 mL each) and the combined organic extracts were dried and stripped in vacuo. The residue was recrystallized from ethyl acetate (~1 liter) to give the first crop of product (11.77 g). The mother liquor was stripped in vacuo and the residue was recrystallized from methanol (~400 mL) to give 3.8 g of 3,5-diiodo-6-methyl-1H-pyridin-2-one. The mother liquor was stripped in vacuo and the residue was recrystallized from EtOAc (~300 mL) with addition of hexanes (200 mL) after most of the product was crystallized to give an additional 9.85 g of 3-iodo-6-methyl-1H-pyridin-2-one. Combined yield: 21.62 g of ≧94% purity, which was carried over to the next reaction.

Part B. 3-(4-Methoxyphenylsulfanyl)-6-methyl-1H-pyridin-2-one

4-Methoxythiophenol (1.7 mL, 13.85 mmol) was added to a suspension of NaH 60% in oil (831 mg, 20.80 mmol) in DMF (30 mL) at 0° C., and the mixture was allowed to warm to 25° C. 3-Iodo-6-methyl-1H-pyridin-2-one (3 g, 12.78 mmol) was added to the solution at 0° C., followed by CuI (533 mg, 2.8 mmol). The reaction was stirred at 25° C. for 1 h and heated at 120° C. for 5 h. Then it was allowed to cool and partitioned between $CH_2Cl_2$ (30 mL) and 9:1 $NH_4Cl/NH_4OH$ (30 mL) and stirred for 15 min. The mixture was extracted with $CH_2Cl_2$ (3×70 mL each) and the combined $CH_2Cl_2$ extracts were washed with water (3×30 mL), brine, dried and stripped in vacuo to give the crude product (3.6 g), which was further purified by washing with ether to give 2.93 g of 3-(4-methoxyphenylsulfanyl)-6-methyl-1H-pyridin-2-one which was used in the next step.

Part C. 2-Chloro-3-(4-methoxyphenylsulfanyl)-6-methylpyridine

The product from part B was heated at reflux in $POCl_3$ (15 mL) for 22 h. The reaction was poured into ice/water (160 mL), and after all the $POCl_3$ had been quenched it was neutralized with $Na_2CO_3$ and extracted with EtOAc (3×100 mL each). The combined organic extracts were dried and stripped in vacuo. The residue was chromatographed on silica gel (20% EtOAc/hexanes eluent) to give 2-chloro-3-(4-methoxyphenylsulfanyl)-6-methylpyridine (2.16 g).

Part D. 2-Chloro-3-(4-methoxybenzenesulfonyl)-6-methylpyridine

2-Chloro-3-(4-methoxyphenylsulfanyl)-6-methylpyridine (1.0 g, 3.76 mmol) was dissolved in CH$_2$Cl$_2$ (40 mL) and cooled to 0° C. m-Chloroperbenzoic acid ~77% max. (1.71 g 7.64 mmol) was added to the solution at 0° C. and the mixture was stirred at 0° C. for 1 h and at 25° C. for 20 h. The reaction was quenched with sat Na$_2$S$_2$O$_5$ (10 mL), sat NaHCO$_3$ was added (20 mL) and the mixture was extracted with CH$_2$Cl$_2$ (40 mL). The combined organic extracts were washed with NaHCO$_3$ (20 mL), dried and stripped in vacuo to give 1.14 g of 2-chloro-3-(4-methoxybenzenesulfonyl)-6-methylpyridine, which was used in the next step without purification.

Part E. [3-(4-Methoxybenzenesulfonyl)-6-methylpyridin-2-yl]-(2,4,6-trimethylphenyl)-amine 2-chloro-3-(4-methoxybenzenesulfonyl)-6-methylpyridine (1.6 g, 5.39 mmol) and 2,4,6-trimethylaniline (4.4 g, 32.8 mmol) were heated at reflux in ethylene glycol (5.5 mL) for 20 h. After cooling, the reaction was partitioned between EtOAc (100 mL) and 0.5 N NaOH (20 mL) and the aqueous layer was extracted with EtOAc (100 mL) and the combined organic extracts were washed with water, brine, dried and stripped in vacuo. The residue was chromatographed on silica gel using 20% EtOAc/hexanes as eluent to give [3-(4-methoxybenzenesulfonyl)-6-methyl-pyridin-2-yl]-(2,4,6-trimethylphenyl)-amine as a solid (1.4 g), mp 165–167° C. mass spec. (AP+): m/z 397 (M+1).

Example 10

4-[6-Methyl-2-(2,4,6-trimethylphenylamino)-pyridine-3-sulfonyl]-phenol

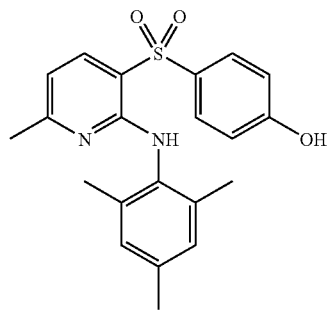

[3-(4-Methoxybenzenesulfonyl)-6-methyl-pyridin-2-yl]-(2,4,6-trimethylphenyl)-amine from Example 9 (3.0 g, 7.57 mmol) was heated in 48% HBr (40 mL) at 110° C. for 48 h. After cooling it was diluted with water (100 mL) and neutralized with Na$_2$CO$_3$. Then it was extracted with EtOAc (3×100 mL each) and the combined organic extracts were dried and stripped in vacuo. The residue was washed with ether to give 4-[6-methyl-2-(2,4,6-trimethylphenylamino)-pyridine-3-sulfonyl]-phenol as a solid (2.6 g), mp 226–228° C. mass spec. (AP+): m/z 383 (M+1).

Example 11

[3-(4-Benzyloxybenzenesulfonyl)-6-methylpyridin-2-yl]-(2,4,6-trimethylphenyl)-amine

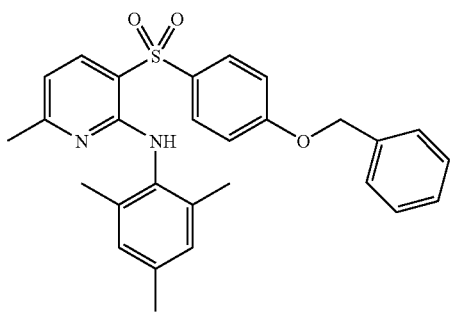

4-[6-Methyl-2-(2,4,6-trimethylphenylamino)-pyridine-3-sulfonyl]-phenol from Example 10 (300 mg, 0.78 mmol), benzyl bromide (0.10 mL, 0.84 mmol), K$_2$CO$_3$ (129 mg, 0.93 mmol) and NaI (20 mg, 0.13 mmol) was heated at reflux in acetonitrile (5 mL) for 15 h. Then it was diluted with EtOAc (15 mL), filtered through florisil and the filtrate was stripped in vacuo. The residue was chromatographed on silica gel using 20% EtOAc/hexanes as eluent to give the product as a solid (340 mg), mp 158–160° C. mass spec. (AP+): m/z 473 (M+1).

Example 12

[3-(4-Ethoxybenzenesulfonyl)-6-methylpyridin-2-yl]-(2,4,6-trimethylphenyl)-amine

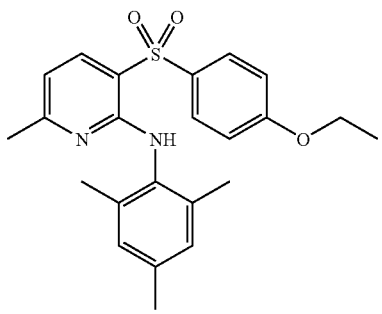

Prepared by the method described in Example 11 using the appropriate starting materials to give the desired product as a solid, 65% yield, mp 157–159° C. mass spec. (AP+): m/z 411 (M+1).

Example 13

[3-(4-Allyloxybenzenesulfonyl)-6-methylpyridin-2-yl]-(2,4,6-trimethylphenyl)-amine

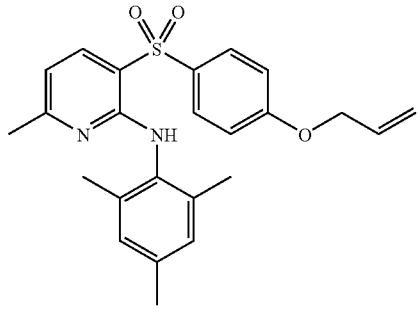

Prepared by the method described in Example 11 using the appropriate starting materials to give the desired product as a solid, 56% yield, mp 138–140° C. Mass spec. (AP+): m/z 432 (M+1).

Example 14

4-{4-[6-Methyl-2-(2,4,6-trimethylphenylamino)-pyridine-3-sulfonyl]-phenoxy}-butyronitrile

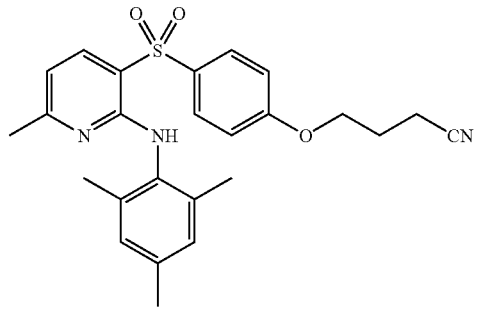

Prepared by the method described in Example 11 using the appropriate starting materials to give the desired product as a solid, 53% yield, mp 160–162° C. Mass spec. (AP+): m/z 450 (M+1).

Example 15

5-{4-[6-Methyl-2-(2,4,6-trimethylphenylamino)-pyridine-3-sulfonyl]-phenoxy}-pentanenitrile

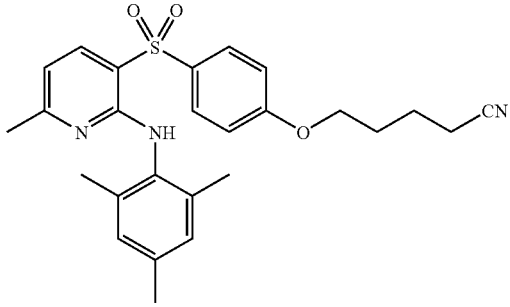

Prepared by the method described in Example 11 using the appropriate starting materials to give the desired product as a solid, 53% yield, mp 115–116° C. Mass spec. (AP+): m/z 464 (M+1).

Example 16

3-{4-[6-Methyl-2-(2,4,6-trimethylphenylamino)-pyridine-3-sulfonyl]-phenoxy}-propan-1-ol

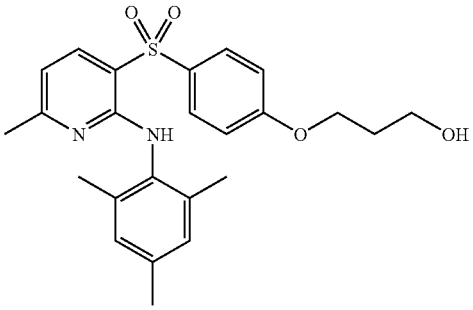

Prepared by the method described in Example 11 using the appropriate starting materials to give the desired product as a solid, 51% yield, mp 152–153° C. Mass spec. (AP+): m/z 441 (M+1).

Example 17

{4-[6-Methyl-2-(2,4,6-trimethylphenylamino)-pyridine-3-sulfonyl]-phenoxy}-acetic acid ethyl ester

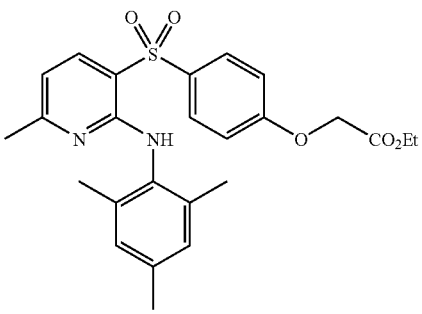

Prepared by the method described in Example 11 using the appropriate starting materials to give the desired product as a solid, 59% yield, mp 116–118° C. Mass spec. (AP+): m/z 469 (M+1).

Example 18

2-{4-[6-Methyl-2-(2,4,6-trimethylphenylamino)-pyridine-3-sulfonyl]-phenoxy}-butyric acid methyl ester

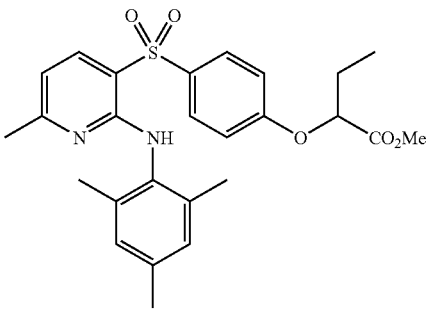

Prepared by the method described in Example 11 using the appropriate starting materials to give the desired product as a solid, 57% yield, mp 111–113° C. Mass spec. (AP+): m/z 483 (M+1).

Example 19

{6-Methyl-3-[4-(pyridin-2-ylmethoxy)-benzene-sulfonyl]-pyridin-2-yl}-(2,4,6-trimethylphenyl)-amine

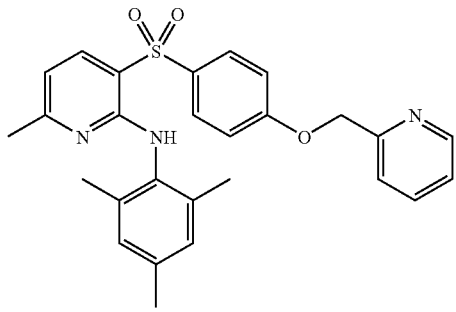

Prepared by the method described in Example 11 using the appropriate starting materials to give the desired product as a solid, mp 182–184° C. Mass spec. (AP+): m/z 474 (M+1).

Example 20

{3-[4-(2,6-Dichloropyridin-4-ylmethoxy)-benzene-sulfonyl]-6-methylpyridin-2-yl}-(2,4,6-trimethylphenyl)-amine

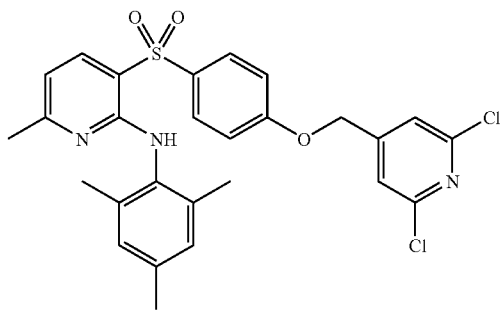

Prepared by the method described in Example 11 using the appropriate starting materials to give the desired product as a solid, mp 192–201° C. Mass spec. (AP+): m/z 542 (M+1).

Example 21

{6-Methyl-3-[4-(2-methylthiazol-4-ylmethoxy)-benzenesulfonyl]-pyridin-2-yl}-(2,4,6-trimethylphenyl)-amine

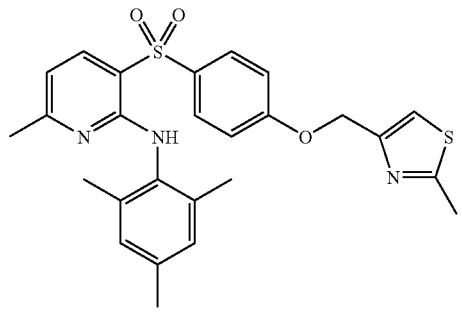

Prepared by the method described in Example 11 using the appropriate starting materials to give the desired product as a solid, mp 200–201° C. Mass spec. (AP+): m/z 494 (M+1).

Example 22

{3-[4-(4-Fluorobenzyloxy)-benzenesulfonyl]-6-methylpyridin-2-yl}-(2,4,6-trimethylphenyl)-amine

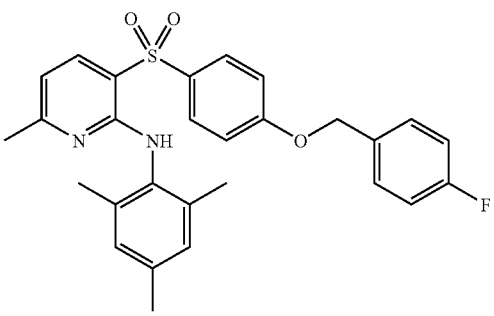

Prepared by the method described in Example-11 using the appropriate starting materials to give the desired product as a solid, mp 178–180° C. Mass spec. (AP+): m/z 491 (M+1).

Example 23

4-{4-[6-Methyl-2-(2,4,6-trimethylphenylamino)-pyridine-3-sulfonyl]-phenoxymethyl}-benzonitrile

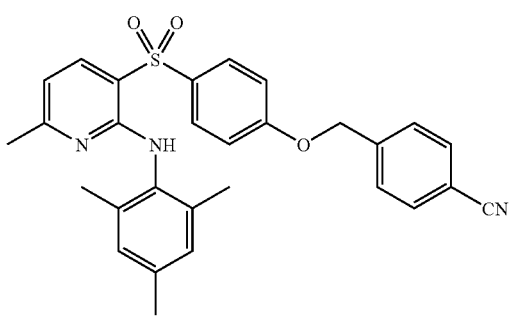

Prepared by the method described in Example 11 using the appropriate starting materials to give the desired product as a solid, mp 208–210° C. Mass spec. (AP+): m/z 498 (M+1).

Example 24

3-{4-[6-Methyl-2-(2,4,6-trimethylphenylamino)-pyridine-3-sulfonyl]-phenoxymethyl}-benzonitrile

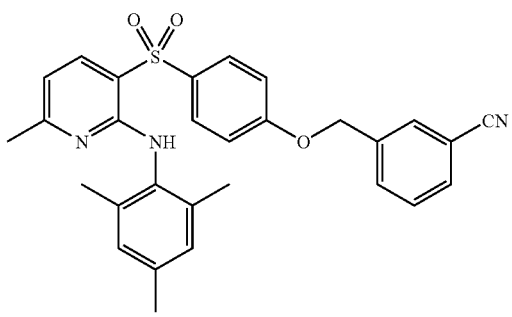

Prepared by the method described in Example 11 using the appropriate starting materials to give the desired product as a solid, 76% yield, mp 155–158° C. Mass spec. (AP+): m/z 498 (M+1).

Example 25

3-{4-[6-Methyl-2-(2,4,6-trimethylphenylamino)-pyridine-3-sulfonyl]-phenoxymethyl}-benzoic acid methyl ester

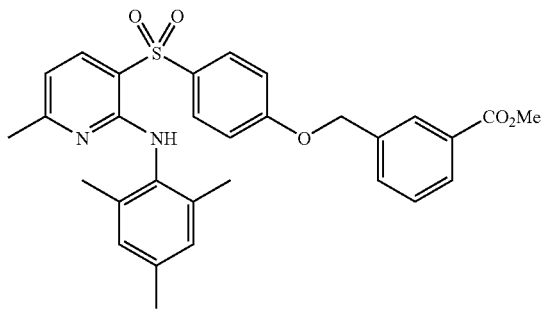

Prepared by the method described in Example 11 using the appropriate starting materials to give the desired product as a solid, 49% yield, mp 148–150° C. Mass spec. (AP+): m/z 531 (M+1).

Example 26

{3-[4-(3-Methoxybenzyloxy)-benzenesulfonyl]-6-methylpyridin-2-yl}-(2,4,6-trimethylphenyl)-amine

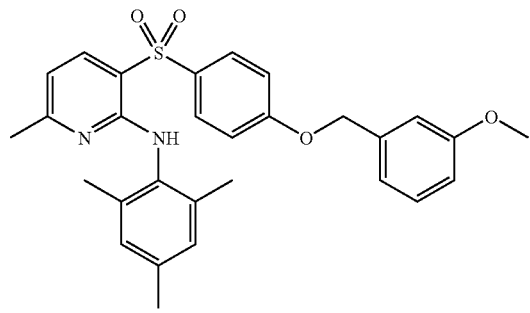

Prepared by the method described in Example 11 using the appropriate starting materials to give the desired product as a solid, mp 124–126° C. Mass spec. (AP+): m/z 503 (M+1).

Example 27

{3-[4-(2-Methoxybenzyloxy)-benzenesulfonyl]-6-methylpyridin-2-yl}-(2,4,6-trimethylphenyl)-amine

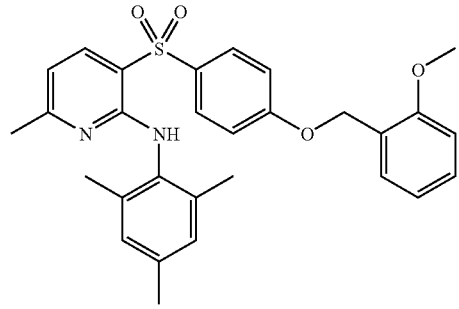

Prepared by the method described in Example 11 using the appropriate starting materials to give the desired product as a solid, 10% yield, mp 148–150° C. Mass spec. (AP+): m/z 503 (M+1).

Example 28

2-{4-[6-Methyl-2-(2,4,6-trimethylphenylamino)-pyridine-3-sulfonyl]-phenoxymethyl}-benzonitrile

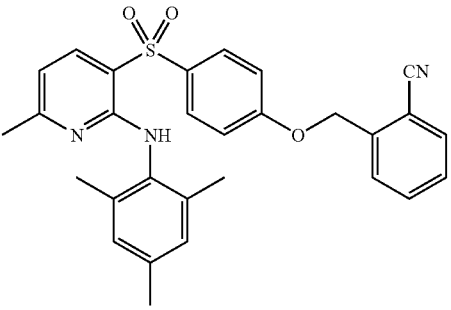

Prepared by the method described in Example 11 using the appropriate starting materials to give the desired product as a solid, mp 208–210° C. Mass spec. (AP+): m/z 498 (M+1).

Example 29

{6-Methyl-3-[4-(2-nitrobenzyloxy)-benzenesulfonyl]-pyridin-2-yl}-(2,4,6-trimethylphenyl)-amine

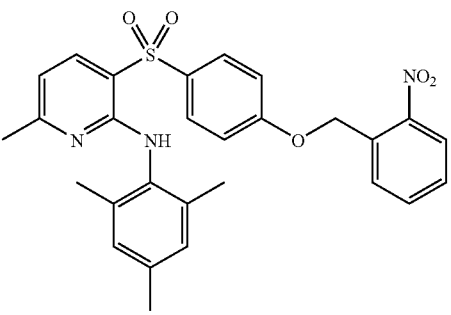

Prepared by the method described in Example 11 using the appropriate starting materials to give the desired product as a solid, mp 153–155° C. Mass spec. (AP+): m/z 518 (M+1).

Example 30

{3-[4-(3,5-Dimethoxybenzyloxy)-benzenesulfonyl]-6-methyl-pyridin-2-yl}-(2,4,6-trimethylphenyl)-amine

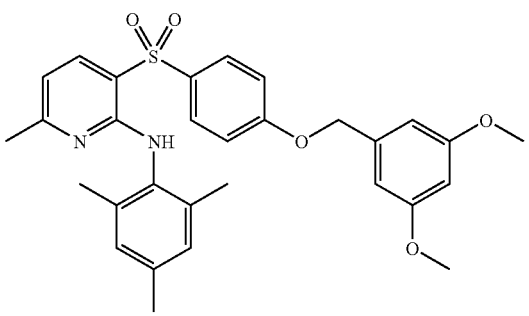

Prepared by the method described in Example 11 using the appropriate starting materials to give the desired product as a solid, mp 107–109° C. Mass spec. (AP+): m/z 533 (M+1).

Example 31

{3-[4-(2,5-Dimethoxybenzyloxy)-benzenesulfonyl]-6-methyl-pyridin-2-yl}-(2,4,6-trimethylphenyl)-amine

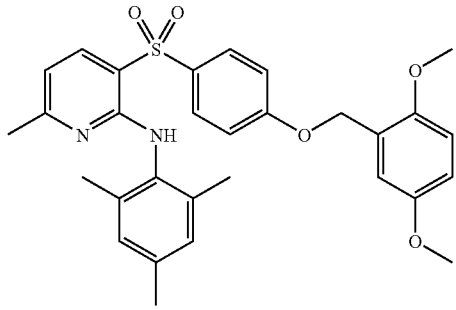

Prepared by the method described in Example 11 using the appropriate starting materials to give the desired product as a solid, mp 128–130° C. Mass spec. (AP+): m/z 533 (M+1).

Example 32

{3-[4-(2,3-Dimethoxybenzyloxy)-benzenesulfonyl]-6-methylpyridin-2-yl}-(2,4,6-trimethylphenyl)-amine

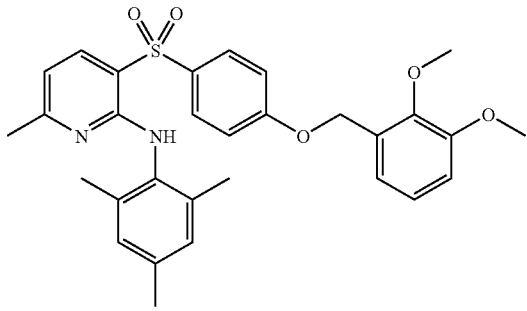

Prepared by the method described in Example 11 using the appropriate starting materials to give the desired product as a solid, mp 124–126° C. Mass spec. (AP+): m/z 533 (M+1).

Example 33

{3-[4-(2,3-Difluorobenzyloxy)-benzenesulfonyl]-6-methylpyridin-2-yl}-(2,4,6-trimethylphenyl)-amine

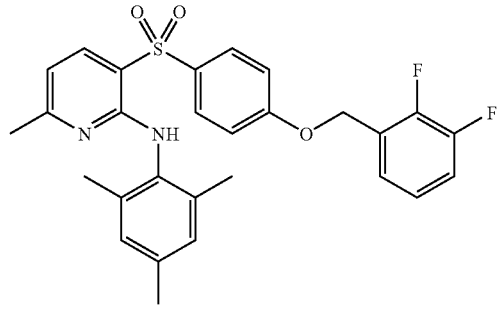

Prepared by the method described in Example 11 using the appropriate starting materials to give the desired product as a solid, mp 136–138° C. Mass spec. (AP+): m/z 509 (M+1).

Example 34

{3-[4-(2-Fluoro-6-nitrobenzyloxy)-benzenesulfonyl]-6-methyl-pyridin-2-yl}-(2,4,6-trimethylphenyl)-amine

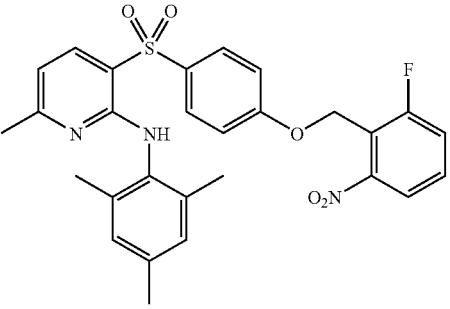

Prepared by the method described in Example 11 using the appropriate starting materials to give the desired product as a solid, mp 132–134° C. Mass spec. (AP+): m/z 536 (M+1).

Example 35

1-(4-Fluoro-3-{4-[6-methyl-2-(2,4,6-trimethylphenylamino)-pyridine-3-sulfonyl]-phenoxymethyl}-phenyl)-ethanone

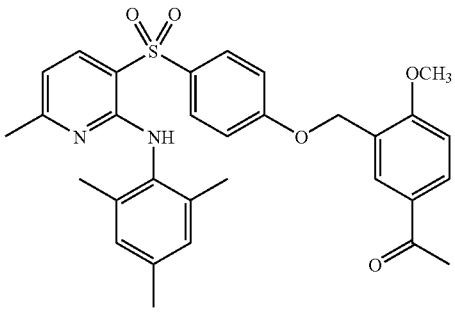

Prepared by the method described in Example 11 using the appropriate starting materials to give the desired product as a solid, mp 141–143° C. Mass spec. (AP+): m/z 545 (M+1).

Example 36

{3-[4-(2,6-Dimethylbenzyloxy)-benzenesulfonyl]-6-methyl-pyridin-2-yl}-(2,4,6-trimethylphenyl)-amine

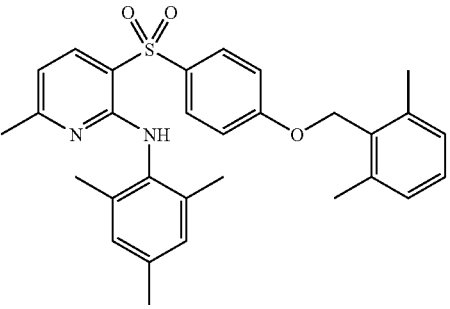

Prepared by the method described in Example 11 using the appropriate starting materials to give the desired product as a solid, mp 136–138° C. Mass spec. (AP+): m/z 501 (M+1).

Example 37

[3-(3-Chloro-4-fluorobenzenesulfonyl)-6-methylpyridin-2-yl]-(2,4,6-trimethylphenyl)-amine

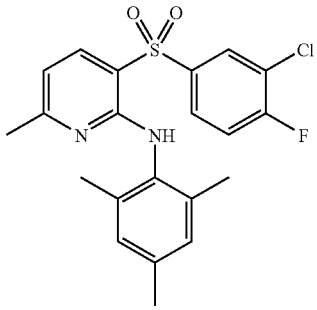

Prepared by the method described in Example 9 using the appropriate starting materials to give the desired product as a solid, mp 139–141° C. mass spec. (AP+): m/z 419 (M+1).

Example 38

[3-(3,4-Dimethylbenzenesulfonyl)-6-methylpyridin-2-yl]-(2,4,6-trimethylphenyl)-amine

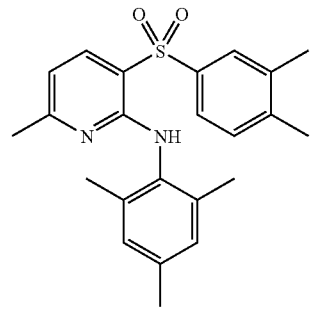

Prepared by the method described in Example 9 using the appropriate starting materials to give the desired product as an oil. mass spec. (AP+): m/z 395 (M+1).

Example 39

[3-(3,4-Dimethoxybenzenesulfonyl)-6-methylpyridin-2-yl]-(2,4,6-trimethylphenyl)-amine

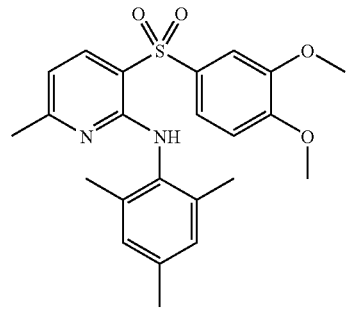

Prepared by the method described in Example 9 using the appropriate starting materials to give the desired product as an amorphous solid. mass spec. (AP+): m/z 427 (M+1).

Example 40

[3-(3,4-Dichlorobenzenesulfonyl)-6-methylpyridin-2-yl]-(2,4,6-trimethylphenyl)-amine

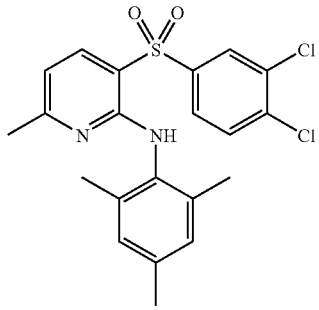

Prepared by the method described in Example 9 using the appropriate starting materials to give the desired product as an amorphous solid. mass spec. (AP+): m/z 435 (M+1).

Example 41

[6-Methyl-3-(toluene-4-sulfonyl)-pyridin-2-yl]-(2,4,6-trimethylphenyl)-amine

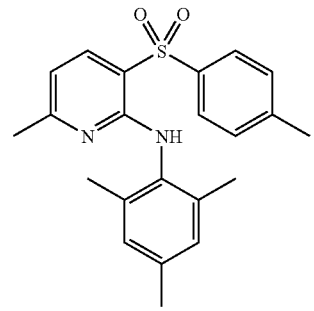

Prepared by the method described in Example 9 using the appropriate starting materials to give the desired product as an oil. mass spec. (AP+): m/z 381 (M+1).

Example 42

[3-(4-Ethylbenzenesulfonyl)-6-methylpyridin-2-yl]-(2,4,6-trimethylphenyl)-amine

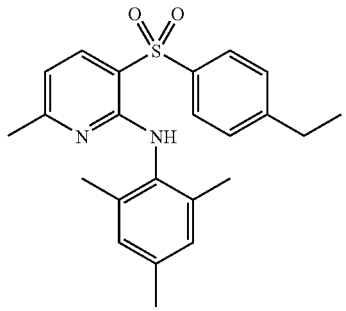

Prepared by the method described in Example 9 using the appropriate starting materials to give the desired product as an amorphous solid. mass spec. (AP+): m/z 395 (M+1).

Example 43

[3-(4-Isopropylbenzenesulfonyl)-6-methylpyridin-2-yl]-(2,4,6-trimethylphenyl)-amine

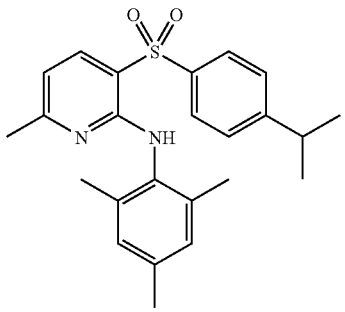

Prepared by the method described in Example 9 using the appropriate starting materials to give the desired product as an amorphous solid. mass spec. (AP+): m/z 409 (M+1).

Example 44

[6-Methyl-3-(4-trifluoromethoxybenzenesulfonyl)-pyridin-2-yl]-(2,4,6-trimethylphenyl)-amine

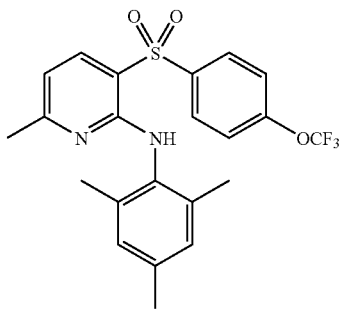

Prepared by the method described in Example 9 using the appropriate starting materials to give the desired product as an amorphous solid. mass spec. (AP+): m/z 451 (M+1).

Example 45

[3-(4-Fluorobenzenesulfonyl)-6-methylpyridin-2-yl]-(2,4,6-trimethylphenyl)-amine

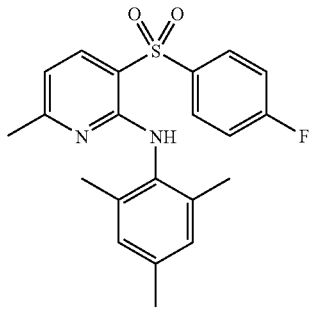

Prepared by the method described in Example 9 using the appropriate starting materials to give the desired product as an amorphous solid. mass spec. (AP+): m/z 385 (M+1).

Example 46

[3-(4-Bromobenzenesulfonyl)-6-methylpyridin-2-yl]-(2,4,6-trimethylphenyl)-amine

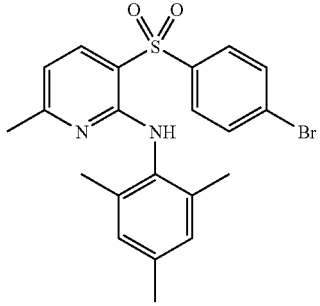

3-(4-Bromobenzenesulfonyl)-2-chloro-6-methylpyridine was synthesized in a similar manner as 2-chloro-3-(4-methoxybenzenesulfonyl)-6-methylpyridine in 32% yield for the three steps. This was coupled with 2,4,6-trimethylaniline in refluxing ethylene glycol to give the title compound in 70% yield after silica gel chromatography (10% EtOAc/hexanes), mp 140–141° C. mass spec. (AP+): m/z 445 (M+1).

Example 47

[3-(4-Ethynylbenzenesulfonyl)-6-methylpyridin-2-yl]-(2,4,6-trimethylphenyl)-amine

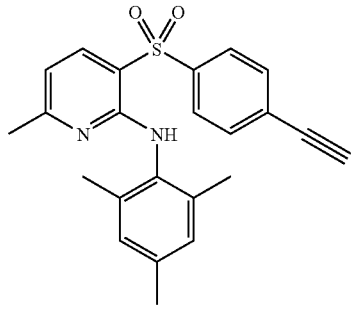

Part A. [6-methyl-3-(4-trimethylsilanylethynyl-benzenesulfonyl)-pyridin-2-yl]-(2,4,6-trimethylphenyl)-amine

[3-(4-Bromobenzenesulfonyl)-6-methylpyridin-2-yl]-(2,4,6-trimethylphenyl)-amine, prepared as described in Example 46, (100 mg, 0.225 mmol), Pd(PPh$_3$)$_2$Cl$_2$ (7.9 mg, 0.011 mmol), CuI (2.1 mg, 0.011 mmol) and trimethylsilylacetylene (0.038 mL, 0.270 mmol) were heated at 50° C. in Et$_3$N (0.5 mL) for 16 h. The reaction mixture was stripped in vacuo and the residue was chromatographed on silica gel using 10% EtOAc/hexanes as eluent to give 53 mg [6-methyl-3-(4-trimethylsilanylethynyl-benzenesulfonyl)-pyridin-2-yl]-(2,4,6-trimethylphenyl)-amine.

Part B. [3-(4-Ethynylbenzenesulfonyl)-6-methylpyridin-2-yl]-(2,4,6-trimethylphenyl)-amine The product from part A was (50 mg, 0.108 mmol) was stirred with K$_2$CO$_3$ (119 mg, 0.865 mmol) in 1 mL CHCl$_3$ and 1 mL MeOH at 25° C. for 16 h. Then the reaction was partitioned between water (20 mL) and CH$_2$Cl$_2$ (100 mL). The organic extract was dried and stripped in vacuo and the residue was purified by silica gel chromatography (10% EtOAc/hexanes eluent) to give the title compound as an amorphous solid (10.5 mg). mass spec. (AP+): m/z 391 (M+1).

Example 48

[3-(Biphenyl-4-sulfonyl)-6-methylpyridin-2-yl]-(2,4,6-trimethylphenyl)-amine

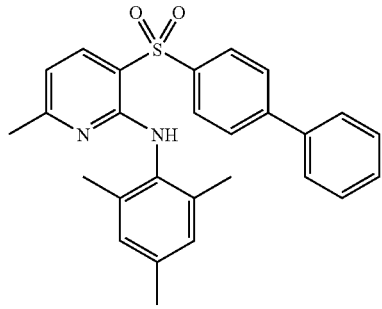

[3-(4-Bromobenzenesulfonyl)-6-methylpyridin-2-yl]-(2,4,6-trimethylphenyl)-amine, prepared as described in Example 46, (100 mg, 0.225 mmol), phenylboronic acid (32.9 mg, 0.269 mmol), Pd(PPh$_3$)$_2$Cl$_2$ (7.7 mg, 0.011 mmol) and Ba(OH)$_2$.8H$_2$O (84.6 mg, 0.269 mmol) were heated at reflux in 1:1 dimethoxyethane/water (2 mL) for 20 h. The reaction was partitioned between EtOAc (100 mL) and water (20 mL) and the organic extract was washed with brine, dried, and stripped in vacuo. The residue was purified by silica gel chromatography (10% EtOAc/hexanes eluent) to give the title compound as a solid (47 mg, 47% yield), mp 140–141° C. mass spec. (AP+): m/z 443 (M+1).

Example 49

[3-(2'-Methoxybiphenyl-4-sulfonyl)-6-methylpyridin-2-yl]-(2,4,6-trimethylphenyl)-amine

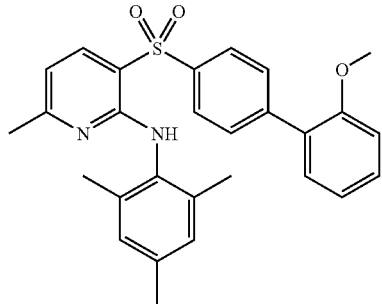

Prepared by the method described in Example 48 using the appropriate starting materials to give the desired product as an amorphous solid. mass spec. (AP+): m/z 473 (M+1).

Example 50

{4-[6-Methyl-2-(2,4,6-trimethylphenylamino)-pyridine-3-sulfonyl]-phenyl}-methanol

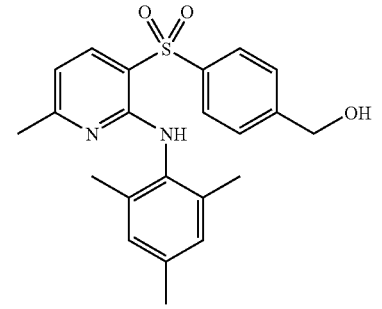

Part A. [4-(2-chloro-6-methylpyridine-3-sulfonyl)-phenyl]-methanol 4-(2-Chloro-6-methylpyridine-3-sulfonyl)-benzoic acid methyl ester, synthesized following the procedure of Example 9 parts A–D in 39% overall yield, (1.29 g, 3.96 mmol) was dissolved in 25 mL of dry ether and cooled to −78° C. To that a 1 M solution of DIBAL-H in hexanes (8.71 mL, 8.71 mmol) was added and the reaction mixture was allowed to warm to 25° C. and stirred for 4 h. The reaction was quenched with water followed by 1 N HCl (40 mL), stirred for 15 min, neutralized with 50% NaOH and extracted with ether and the ether extracts were combined, washed with brine, dried and stripped in vacuo to give 1.15 g of [4-(2-chloro-6-methylpyridine-3-sulfonyl)-phenyl]-methanol.

Part B. {4-[6-Methyl-2-(2,4,6-trimethylphenylamino)-pyridine-3-sulfonyl]-phenyl}-methanol

[4-(2-Chloro-6-methylpyridine-3-sulfonyl)-phenyl]-methanol (1.15 g, 3.86 mmol) and 2,4,6-trimethyl aniline (3.13 g, 23.2 mmol) were heated at reflux in ethylene glycol (3.5 mL) for 16 h. After cooling the mixture was diluted with water (50 mL) and extracted with ethyl acetete (2×200 mL). The combined organic extracts were washed with brine, dried and stripped in vacuo. The residue was purified by column chromatography on silica gel (40% EtOAc/hexanes eluent) to give the product {4-[6-methyl-2-(2,4,6-trimethylphenylamino)-pyridine-3-sulfonyl]-phenyl}-methanol as an amorphous solid (836 mg, 55% yield for the two steps) and (6-methyl-3-{4-[(2,4,6-trimethylphenylamino)-methyl]-benzenesulfonyl}-pyridin-2-yl)-(2,4,6-trimethyl-phenyl)-amine (53 mg, 3.5% yield). mass spec. (AP+): m/z 397 (M+1).

Example 51

(6-Methyl-3-{4-[(2,4,6-trimethylphenylamino)-methyl]-benzenesulfonyl}-pyridin-2-yl)-(2,4,6-trimethylphenyl)-amine

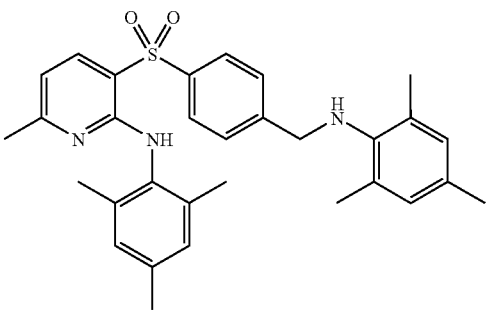

Prepared by the method described in Example 50 to give the title compound as an amorphous solid. mass spec. (AP+): m/z 514 (M+1).

Example 52

4-[6-Methyl-2-(2,4,6-trimethylphenylamino)-pyridine-3-sulfonyl]-benzaldehyde

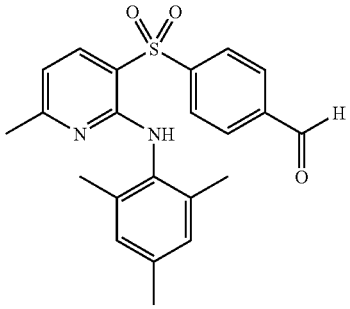

{4-[6-Methyl-2-(2,4,6-trimethylphenylamino)-pyridine-3-sulfonyl]-phenyl}-methanol, prepared as described in Example 50, (0.5 g, 1.26 mmol) was dissolved in CHCl₃ (10 mL) and Dess-Martin periodinane (0.59 g, 1.39 mmol) was added. The reaction was stirred at 25° C. for 16 h, dissolved in EtOAc (100 mL), and the EtOAc was washed with sat sodium thiosulfate solution (20 mL), water (20 mL) and brine, dried and stripped in vacuo. The residue was chromatographed on silica gel using 20% EtOAc/hexanes eluent to give 4-[6-methyl-2-(2,4,6-trimethylphenylamino)-pyridine-3-sulfonyl]-benzaldehyde (472 mg, 95% yield) as an amorphous solid. mass spec. (AP+): m/z 395 (M+1).

Example 53

{4-[6-Methyl-2-(2,4,6-trimethylphenylamino)-pyridine-3-sulfonyl]-phenyl}-phenyl-methanol

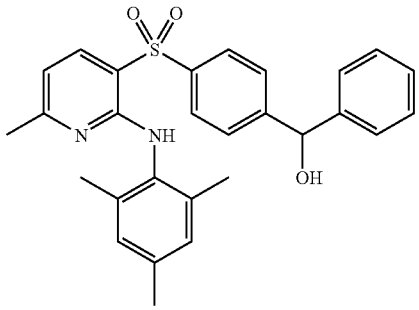

4-[6-Methyl-2-(2,4,6-trimethylphenylamino)-pyridine-3-sulfonyl]-benzaldehyde, prepared as described in Example 52, (100 mg, 0.25 mmol) was dissolved in dry THF and cooled to 0° C. To the solution was added a 1 M solution of PhMgBr in THF (0.63 mL, 0.63 mmol) and the reaction was stirred at 25° C. for 2 h, quenched with water and neutralized with 10% HCl and extracted with EtOAc (100 mL). The EtOAc was washed with brine, dried and stripped in vacuo. The residue was purified by silica gel chromatography (20% EtOAc/hexanes eluent) to give 15 mg {4-[6-methyl-2-(2,4,6-trimethylphenylamino)-pyridine-3-sulfonyl]-phenyl}-phenyl-methanol as an amorphous solid. mass spec. (AP+): m/z 473 (M+1).

Example 54

{4-[6-Methyl-2-(2,4,6-trimethylphenylamino)-pyridine-3-sulfonyl]-phenyl}-phenyl-methanone

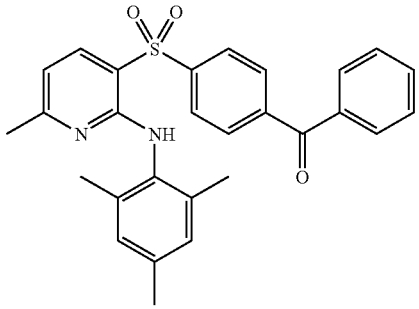

{4-[6-Methyl-2-(2,4,6-trimethylphenylamino)-pyridine-3-sulfonyl]-phenyl}-phenyl-methanol, prepared as described in Example 53, (60 mg, 0.127 mmol) was dissolved in CHCl₃ (2 mL) and Des-Martin periodinane (59 mg, 0.140 mmol) was added. The reaction was stirred at 25° C. for 1.5 h, dissolved in EtOAc (100 mL), and the EtOAc was washed with sat. sodium thiosulfate solution (20 mL), water (20 mL) and brine, dried and stripped in vacuo. The residue was chromatographed on silica gel using 20% EtOAc/hexanes eluent to give {4-[6-methyl-2-(2,4,6-trimethylphenylamino)-pyridine-3-sulfonyl]-phenyl}-phenyl-methanone (59 mg, 99% yield) as a solid, mp 222–225° C. mass spec. (AP+): m/z 471 (M+1).

Example 55

Acetic acid 4-[6-methyl-2-(2,4,6-trimethylphenylamino)-pyridine-3-sulfonyl]-benzyl ester

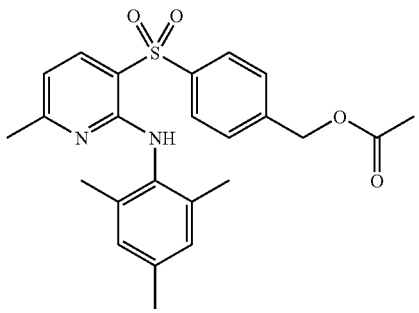

The target compound was prepared by acetylation of {4-[6-methyl-2-(2,4,6-trimethylphenylamino)-pyridine-3-sulfonyl]-phenyl}-methanol, prepared as described in Example 50, using standard conditions to give a solid, mp 132–134° C. mass spec. (AP+): m/z 439 (M+1).

Example 56

[3-(3-Methoxybenzenesulfonyl)-6-methylpyridin-2-yl]-(2,4,6-trimethylphenyl)-amine

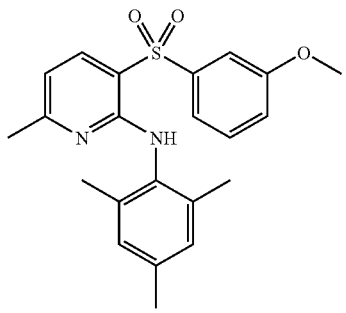

Prepared by the method described in Example 11 using the appropriate starting materials to give the desired product as a solid, mp 87–88° C. mass spec. (AP+): m/z 397 (M+1).

Example 57

3-[6-Methyl-2-(2,4,6-trimethylphenylamino)-pyridine-3-sulfonyl]-phenol

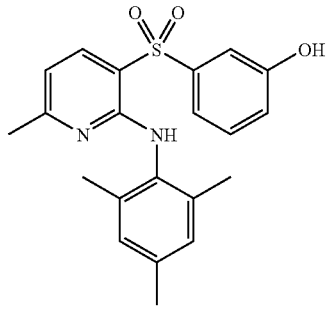

Prepared by the method described in Example 10 using the appropriate starting materials to give the desired product as a solid, mp 196–197° C. mass spec. (AP+): m/z 383 (M+1).

Example 58

[3-(3-Ethoxybenzenesulfonyl)-6-methylpyridin-2-yl]-(2,4,6-trimethylphenyl)-amine

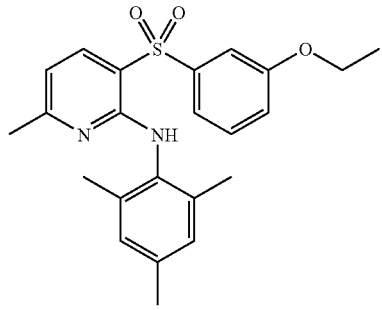

Prepared by the method described in Example 11 using the appropriate starting materials to give the desired product as a solid, mp 96–97° C. mass spec. (AP+): m/z 411 (M+1).

Example 59

[3-(3-Allyloxybenzenesulfonyl)-6-methylpyridin-2-yl]-(2,4,6-trimethylphenyl)-amine

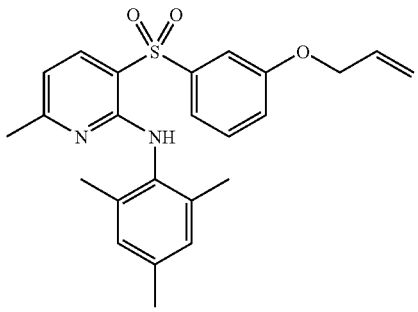

Prepared by the method described in Example 11 using the appropriate starting materials to give the desired product as an amorphous solid. mass spec. (AP+): m/z 423 (M+1).

Example 60

[3-(3-Benzyloxybenzenesulfonyl)-6-methylpyridin-2-yl]-(2,4,6-trimethylphenyl)-amine

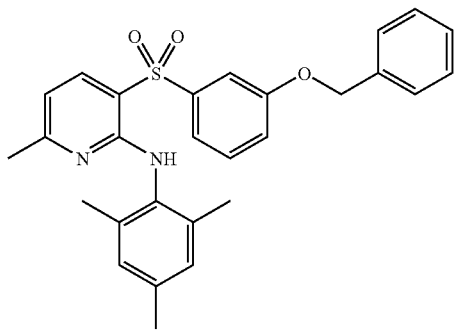

Prepared by the method described in Example 11 using the appropriate starting materials to give the desired product as an amorphous solid. mass spec. (AP+): m/z 473 (M+1).

Example 61

{3-[3-(4-Fluorobenzyloxy)-benzenesulfonyl]-6-methylpyridin-2-yl}-(2,4,6-trimethylphenyl)-amine

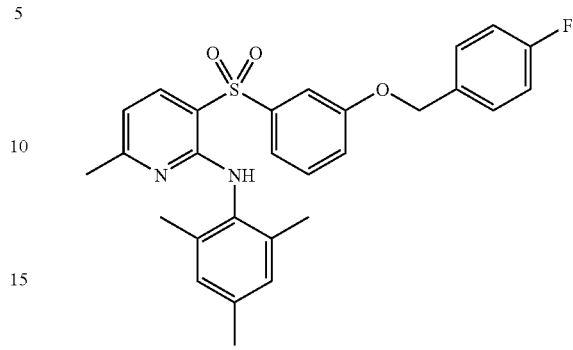

Prepared by the method described in Example 11 using the appropriate starting materials to give the desired product as an amorphous solid. mass spec. (AP+): m/z 491 (M+1).

Example 62

{3-[3-(3-Methoxybenzyloxy)-benzenesulfonyl]-6-methylpyridin-2-yl}-(2,4,6-trimethylphenyl)-amine

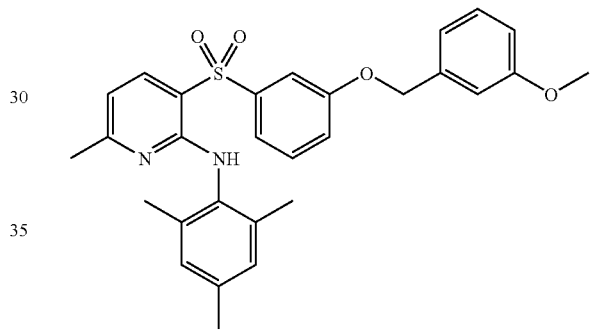

Prepared by the method described in Example 11 using the appropriate starting materials to give the desired product as an amorphous solid. mass spec. (AP+): m/z 503 (M+1).

Example 63

{3-[3-(3,5-Dimethoxybenzyloxy)-benzenesulfonyl]-6-methylpyridin-2-yl}-(2,4,6-trimethylphenyl)-amine

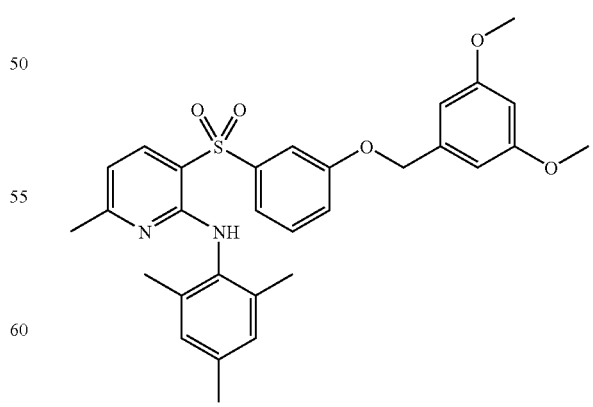

Prepared by the method described in Example 11 using the appropriate starting materials to give the desired product as a solid, mp 120–121° C. mass spec. (AP+): m/z 533 (M+1).

Example 64

{3-[3-(6-Chloropyridin-3-ylmethoxy)-benzenesulfonyl]-6-methylpyridin-2-yl}-(2,4,6-trimethylphenyl)-amine

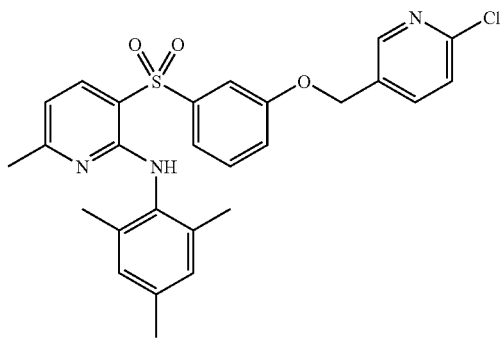

Prepared by the method described in Example 11 using the appropriate starting materials to give the desired product as an amorphous solid. mass spec. (AP+): m/z 508 (M+1).

Example 65

{3-[3-(2,6-Dichloropyridin-4-ylmethoxy)-benzenesulfonyl]-6-methylpyridin-2-yl}-(2,4,6-trimethylphenyl)-amine

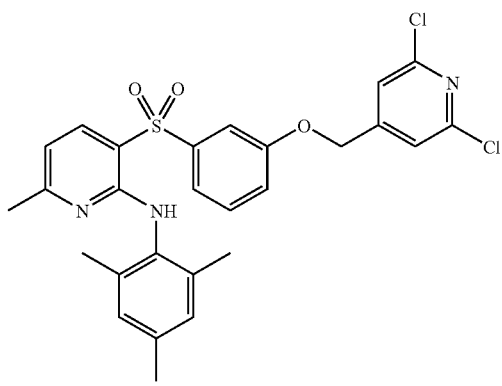

Prepared by the method described in Example 11 using the appropriate starting materials to give the desired product as an amorphous solid. mass spec. (AP+): m/z 542 (M+1).

Example 66

(2,4-Dimethylphenyl)-[3-(4-ethylbenzenesulfonyl)-6-methylpyridin-2-yl]-amine

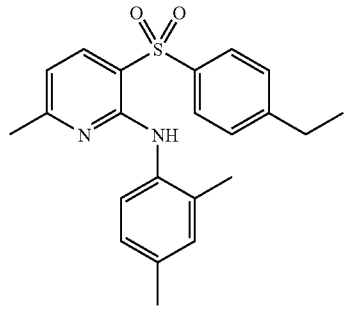

Prepared by the method described in Example 9 using the appropriate starting materials to give the desired product as an oil. mass spec. (AP+): m/z 381 (M+1).

Example 67

[3-(4-Ethylbenzenesulfonyl)-6-methylpyridin-2-yl]-(4-methoxy-2-methylphenyl)-amine

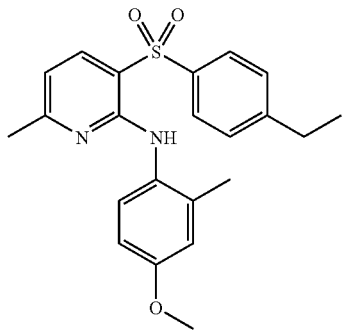

Prepared by the method described in Example 9 using the appropriate starting materials to give the desired product as an oil. mass spec. (AP+): m/z 397 (M+1).

Example 68

(2,4-Dimethoxyphenyl)-[3-(4-ethylbenzenesulfonyl)-6-methylpyridin-2-yl]-amine

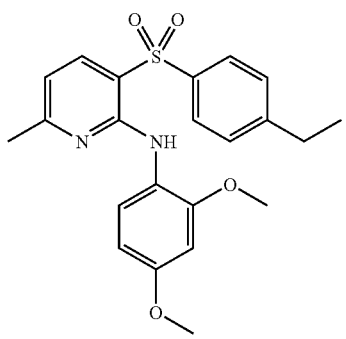

Prepared by the method described in Example 9 using the appropriate starting materials to give the desired product as an oil. mass spec. (AP+): m/z 413 (M+1).

Example 69

(2-Chloro-4-methoxyphenyl)-[3-(4-ethylbenzenesulfonyl)-6-methylpyridin-2-yl]-amine

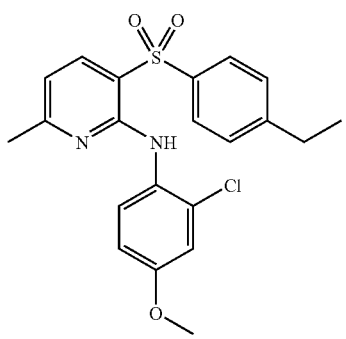

Prepared by the method described in Example 9 using the appropriate starting materials to give the desired product as a solid, mp 110–112° C. mass spec. (AP+): m/z 417 (M+1).

Example 70

[3-(4-Ethylbenzenesulfonyl)-6-methylpyridin-2-yl]-(2,4,5-trimethylphenyl)-amine

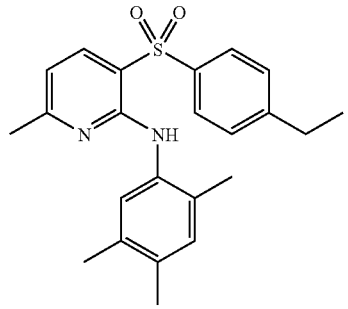

Prepared by the method described in Example 9 using the appropriate starting materials to give the desired product as an oil. mass spec. (AP+): m/z 395 (M+1).

UTILITY

CRF-R1 Receptor Binding Assay for the Evaluation of Biological Activity

The following is a description of the isolation of cell membranes containing cloned human CRF-R1 receptors for use in a standard binding assay as well as a description of the assay itself.

Messenger RNA was isolated from human hippocampus. The mRNA was isolated from human hippocampus. The mRNA was reverse transcribed using oligo (dt) 12–18 and the coding region was amplifies by PCR from start to stop codons. The resulting PCR fragment was cloned into the EcoRV site of pGEMV, from whence the insert was reclaimed using XhoI+XbaI and cloned into the XhoI+XbaI sites of vector pm3 as (which contains a CMV promoter, the SV't' splice and early poly A signals, an Eptein-Barr viral origin of replication, and a hygromycin selectable marker). The resulting expression vector, called phchCRFR was transfected in 293EBNA cells and cells retaining the episome were selected in the presence of 400 µM hygromycin. Cells surviving 4 weeks of selection in hygromycin were pooled, adapted to growth in suspension and used to generate membranes for the binding assay described below. Individual aliquots containing approximately $1 \times 10^8$ of the suspended cells were then centrifuged to form a pellet and frozen. For the binding assay a frozen pellet described above containing 293EBNA cells transfected with hCRFR1 receptors is homogenized in 10 mL of ice cold tissue buffer (50 mM HEPES buffer pH 7.0, containing 10 MM $MgCl_2$, 2 mM EGTA, 1 µg/mL apotinin, 1 µg/mL leupeptin and 1 µg/mL pepstatin). The homoginate is centrifuged at 40,000×g for 12 min and the resulting pellet rehomogenized in 10 mL of tissue buffer. After another centrifugation at 40,000×g for 12 min, the pellet is resuspended to a protein concentration of 360 µg/mL to be used in the assay.

Binding assays are performed in 96 well plates; each well having a 300 µL capacity. To each well is added 50 µL of test drug dilutions (final concentration of drugs range from $10^{-10}$–$10^{-5}$ M), 100 µL of $^{125}$I-ovine-CRF ($^{125}$I-o-CRF) (final concentration 150 pM) and 150 µL of the cell homoginate described above. Plates are then allowed to incubate at room temperature for 2 hours before filtering the incubate over GF/F filters (presoaked with 0.3% polyethyleneimine) using an appropriate cell harvester. Filters are rinsed 2 times with ice cold assay buffer before removing individual filters and assessing them for radioactivity on a gamma counter.

Curves of the inhibition of $^{125}$I-o-CRF binding to cell membranes at various dilutions of test drug are analyzed by the iterative curve fitting program LIGAND [P. J. Munson and D. Rodbard, *Anal. Biochem.*, 107:220 (1980), which provides $K_i$ values for inhibition which are then used to assess biological activity.

A compound is considered to be active if it has a $K_i$ value of less than about 10,000 nM for the inhibition of CRF. Preferred compounds have a $K_i$ value of less than about 1000 nM for the inhibition of CRF. More preferred compounds have a $K_i$ values of less than about 100 nM for the inhibition of CRF.

Compounds of the present invention have demonstrated a $K_i$ value of less than about 10,000 nM for the inhibition of CRF in the CRF-R1 Receptor Binding Assay for the evaluation of biological activity.

Alternate CRF-R1 Receptor Binding Assay for the Evaluation of Biological Activity.

The following is a description of the isolation of cell membranes containing cloned human CRF-R1 receptors for use in a standard binding assay as well as a description of the assay itself.

Messenger RNA was isolated from human hippocampus. The mRNA was isolated from human hippocampus. The mRNA was reverse transcribed using oligo (dt) 12–18 and the coding region was amplifies by PCR from start to stop codons. The resulting PCR fragment was cloned into the EcoRV site of pGEMV, from whence the insert was reclaimed using XhoI+XbaI and cloned into the XhoI+XbaI sites of vector pm3 as (which contains a CMV promoter, the SV't' splice and early poly A signals, an Eptein-Barr viral origin of replication, and a hygromycin selectable marker). The resulting expression vector, called phchCRFR was transfected in 293EBNA cells and cells retaining the episome were selected in the presence of 400 µM hygromycin. Cells surviving 4 weeks of selection in hygromycin were pooled, adapted to growth in suspension and used to generate membranes for the binding assay described below.

HEK 293 EBNA-1 cells (HEK 293E, Invitrogen, CA), were transfected with a vector encoding the human CRF-R1 gene using a standard calcium phosphate protocol. The vector sequence included the oriP origin of replication, which permits episomal maintenance in cells expressing the EBNA-1 gene, and the gene for hygromycin resistance. Following transfection, cells were pooled and plated into a medium containing hygromycin for the selection of cells expressing CRF-R1. After isolation, the cell pool CL0138 was assessed in radioligand binding and functional-based assays. These cells are maintained in Dulbecco's Modified Eagle medium (DMEM) containing 10% v/v fetal bovine serum (FBS), 2 mM L-glutamine and 400 µg/mL hygromycin. Cell pellets prepared from this cell line were used in $CRF_1$ competition binding assays. Individual aliquots containing approximately $1 \times 10^8$ of the suspended cells were then centrifuged to form a pellet, frozen and stored at −80° C.

A frozen pellet described above containing 293EBNA cells transfected with hCRFR1 receptors or the rat frontal cortex tissue dissected from frozen rat brains was prepared as the source of membranes expressing CRF1 receptors used in binding assays. Tissue or pellets of whole cells were thawed on ice and homogenized in tissue buffer (containing 50 mM HEPES, 10 mM $MgCl_2$, 2 mM EGTA, and 1 µg/mL each of aprotonin, leupeptin, and pepstatin, pH 7.0 @ 23° C.) using a Brinkman Polytron (PT-10, setting 6 for 10 seconds). The homogenate was centrifuged at 48,000×g for 12 min and the resulting pellet was washed by double re-suspension and centrifugation steps. Membranes from rat frontal cortex were prepared similarly except for the inclusion of an additional wash/centrifugation cycle. The final pellet was suspended in tissue buffer, and protein concentrations were determined using the bicinchoninic acid (BCA) assay (Pierce, Rockford, Ill.) with bovine serum albumin as standard.

Equilibrium competition binding experiments were performed using a modification of the methods described previously to determine binding affinities of compounds at $CRF_1$ (Arvanitis et al., 1999). All small molecule ligands were initially prepared in 100% DMSO at a concentration of $10^{-2}$ M and diluted in assay buffer that was identical to the tissue buffer except for the inclusion of 0.15 mM bacitracin and 0.1% w/v ovalbumin. Competition assays were conducted in disposable polypropylene 96-well plates (Costar Corp., Cambridge, Mass.), in a total volume of 300 µL. The reaction was initiated by the addition of 50 µL of competing compounds in 12 concentrations (final concentrations ranging from $10^{-11}$ to $10^{-5}$ M), 100 µL assay buffer containing the radioligand [$^{125}$I]ovine CRF (final concentration 150 pM), and 150 µL membrane homogenate (containing 5–10 µg protein). The reaction mixtures were incubated to equilibrium for 2 h at 23° C. Specific binding was defined in the presence of 10 µM DMP 696 or SC241 for $CRF_1$ receptors. Binding assays were terminated by rapid filtration over GF/C glass-fibers (pre-soaked in 0.3% v/v polyethyleneimine) using a 96-well cell harvester followed by three washes with 0.3 mL cold wash buffer (PBS, pH 7.0, containing 0.01% Triton X-100). The filter was dried, and counted in a gamma counter or a 96-well Top Counter at 80% efficiency. The $CRF_1$ competition binding to membranes from rat frontal cortex were performed similarly except for the radioligand concentration of [$^{125}$I]ovine (final concentration approximately 200 pM) and membrane protein (40–65 µg/well) used in the binding.

The inhibition of [$^{125}$I]ovine CRF binding to cell membranes by increasing concentrations of test drugs are analyzed by fitting data through the competition equation in the iterative nonlinear regression curve-fitting programs Prism (GraphPad Prism, San Diego, Calif.) to determine binding affinities ($IC_{50}$'s or $K_i$'s) of ligands for $CRF_1$ receptors. A compound is considered to be active if it has a $K_i$ value of less than about 10,000 nM for the inhibition of [$^{125}$I]ovine CRF binding.

Inhibition of CRF-Stimulated Adenylate Cyclase Activity

Inhibition of CRF-stimulated adenylate cyclase activity can be performed as described by G. Battaglia et al., Synapse, 1:572 (1987). Briefly, assays are carried out at 37° C. for 10 min in 200 ml of buffer containing 100 mM Tris-HCl (pH 7.4 at 37° C.), 10 mM $MgCl_2$, 0.4 mM EGTA, 0.1% BSA, 1 mM isobutylmethylxanthine (IBMX), 250 units/ml phosphocreatine kinase, 5 mM creatine phosphate, 100 mM guanosine 5'-triphosphate, 100 nM oCRF, antagonist peptides (concentration range $10^{-9}$ to $10^{-6m}$) and 0.8 mg original wet weight tissue (approximately 40–60 mg protein). Reactions are initiated by the addition of 1 mM ATP/[$^{32}$P]ATP (approximately 2–4 mCi/tube) and terminated by the addition of 100 ml of 50 mM Tris-HCL, 45 mM ATP and 2% sodium dodecyl sulfate. In order to monitor the recovery of cAMP, 1 µl of [$^3$H]cAMP (approximately 40,000 dpm) is added to each tube prior to separation. The separation of [$^{32}$P]CAMP from [$^{32}$P]ATP is performed by sequential elution over Dowex and alumina columns.

In Vivo Biological Assay

The in vivo activity of the compounds of the present invention can be assessed using any one of the biological assays available and accepted within the art. Illustrative of these tests includes the Acoustic Startle Assay, the Stair Climbing Test, and the Chronic Administration Assay. These and other models useful for the testing of compounds of the present invention have been outlined in C. W. Berridge and A. J. Dunn, Brain Research Reviews, 15:71 (1990). Compounds may be tested in any species of rodent or small mammal.

Compounds of this invention have utility in the treatment of imbalances associated with abnormal levels of corticotropin releasing factor in patients suffering from depression, affective disorders, and/or anxiety.

Compounds of this invention can be administered to treat these abnormalities by means that produce contact of the active agent with the agent's site of action in the body of a mammal. The compounds can be administered by any conventional means available for use in conjunction with pharmaceuticals either as individual therapeutic agent or in combination of therapeutic agents. They can be administered alone, but will generally be administered with a pharmaceutical carrier selected on the basis of the chosen route of administration and standard pharmaceutical practice.

The dosage administered will vary depending on the use and known factors such as pharmacodynamic character of the particular agent, and its mode and route of administration; the recipient's age, weight, and health; nature and extent of symptoms; kind of concurrent treatment; frequency of treatment; and desired effect. For use in the treatment of said diseases or conditions, the compounds of this invention can be orally administered daily at a dosage of the active ingredient of 0.002 to 200 mg/kg of body weight. Ordinarily, a dose of 0.01 to 10 mg/kg in divided doses one to four times a day, or in sustained release formulation will be effective in obtaining the desired pharmacological effect.

Dosage forms (compositions) suitable for administration contain from about 1 mg to about 100 mg of active ingredient per unit. In these pharmaceutical compositions, the active ingredient will ordinarily be present in an amount of about 0.5 to 95% by weight based on the total weight of the composition.

The active ingredient can be administered orally is solid dosage forms, such as capsules, tablets and powders; or in liquid forms such as elixirs, syrups, and/or suspensions. The compounds of this invention can also be administered parenterally in sterile liquid dose formulations.

The compounds of this invention may also be used as reagents or standards in the biochemical study of neurological function, dysfunction, and disease.

Although the present invention has been described and exemplified in terms of certain particular embodiments, other embodiments will be apparent to those skilled in the art. The invention is, therefore, not limited to the particular embodiments described and exemplified, but is capable of modification or variation without departing from the spirit of the invention, the full scope of which is delineated by the appended claims.

What is claimed is:

1. A compound of Formula (I)

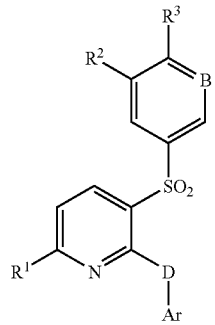

or a pharmaceutically acceptable salt or solvate thereof, wherein

B is CH;

D is NH;

$R^1$ is selected from the group consisting of H, —CN, $C_{1-4}$ alkyl, $C_{3-7}$ cycloalkyl, $C_{2-4}$ alkenyl, $C_{2-4}$ alkynyl, $C_{1-4}$ alkoxy and $N(C_{1-4}$ alkyl$)_2$ optionally and independently substituted with 1 to 3 substituents selected from the group consisting of —CN, hydroxy, halo, $C_{1-4}$ haloalkyl and $C_{1-4}$ alkoxy;

$R^2$ is selected from the group consisting of H, halo, —CN, hydroxy, $C_{1-6}$ alkyl, $C_{2-6}$ alkenyl, $C_{2-6}$ alkynyl, $C_{3-7}$ cycloalkyl, $C_{1-6}$ alkoxy, $C_{1-6}$ haloalkyl, —NR$^4$R$^6$, —$C_{1-6}$alkylNR$^4$R$^6$, —$C_{1-6}$alkylOR$^6$, $CO_2R^6$, $O_2CR^6$, COR6, CON4R6, NR4CO2R6, NR4SO2R6, NR4COR6, OCONR4R6 and NR4CONR5R6; optionally and independently substituted with 1 to 3 substituents selected from the group consisting of —CN, hydroxy, halo, C1–4 haloalkyl, C1–4 alkoxy, CO2C1–4 alkyl or phenyl;

$R^3$ is selected from the group consisting of H, halo, —CN, hydroxy, $C_{1-6}$ alkyl, $C_{2-6}$ alkenyl, $C_{2-6}$ alkynyl, $C_{3-7}$ cycloalkyl, $C_{1-6}$ alkoxy, $C_{1-6}$ haloalkyl, —NR$^4$R$^6$, —$C_{1-6}$alkylNR$^4$R$^6$, —$C_{1-6}$alkylOR$^6$, $CO_2R^6$, $O_2CR^6$, COR$^6$, CON$^4$R$^6$, NR$^4$CO$_2$R$^6$, NR$^4$SO$_2$R$^6$, and NR$^4$COR$^6$; optionally and independently substituted with 1 to 3 substituents selected from the group consisting of —CN, hydroxy, halo, $C_{1-4}$ haloalkyl, $C_{1-4}$ alkoxy, $CO_2C_{1-4}$ alkyl, or phenyl;

Ar is selected from the group consisting of phenyl, indanyl, and indenyl, independently and optionally substituted with 1 to 4 substituents selected from the group consisting of H, $C_{1-6}$ alkyl, $C_{3-6}$ cycloalkyl, $C_{1-4}$ alkoxy-$C_{1-4}$ alkyl, —OR$^4$, halo, $C_{1-4}$ haloalkyl, —CN, —NO$_2$, SH, —S(O)$_2$R$^5$, —COR$^4$, —CO$_2$R$^4$, —OC(O)R$^5$, —N(COR$^4$)$_2$, —NR$^4$R$^7$ and —CONR$^4$R$^7$, —NR$^4$COR$^5$, NR$^4$SO$_2$R$^5$, NR$^4$CONR$^5$R$^7$, and NR$^4$CO$_2$R$^5$;

$R^4$, $R^5$ and $R^7$ are independently selected from the group consisting of H, $C_{1-6}$ alkyl, $C_{3-6}$ cycloalkyl, $C_{3-6}$ cycloalkyl-$C_{3-6}$ alkyl, $C_{1-2}$ alkoxy-$C_{1-4}$ alkyl and $C_{1-4}$ haloalkyl; and $R^6$ is selected from the group consisting of H, $C_{1-6}$ alkyl, $C_{3-6}$ cycloalkyl, $C_{3-6}$ cycloalkyl-$C_{1-6}$ alkyl, $C_{1-2}$ alkoxy-$C_{1-2}$ alkyl, $C_{1-4}$ haloalkyl, phenyl and $C_{1-6}$ alkyl-phenyl.

2. A compound according to claim 1 wherein $R^1$ is $C_{1-4}$ alkyl.

3. A compound according to claim 1 wherein $R^2$ is H, halo, hydroxy, $C_{1-6}$ alkyl, $C_{1-6}$ alkoxy, morpholinyl, piperazinyl or phenyl.

4. A compound according to claim 1 wherein $R^3$ is H, halo, —CN, hydroxy, $C_{1-6}$ alkyl, $C_{2-6}$ alkynyl, $C_{1-6}$ alkoxy, $C_{1-6}$ haloalkyl, —NR$^4$R$^6$, morpholinyl, piperazinyl or phenyl.

5. A compound according to claim 1 wherein Ar is phenyl, independently and optionally substituted with 1 to 4 substituents selected from the group consisting of H, $C_{1-6}$ alkyl, —OR$^4$, halo, —CN, —NO$_2$, —CO$_2$R$^4$.

6. A compound according to claim 1 wherein $R^4$, $R^5$ and $R^7$ are independently H or $C_{1-6}$ alkyl.

7. A compound according to claim 1 wherein $R^6$ is H.

8. A compound according to claim 1 wherein B is CH; D is NH; $R^1$ is $C_{1-4}$ alkyl; $R^2$ is H, halo, hydroxy, $C_{1-6}$ alkyl, $C_{1-6}$ alkoxy, morpholinyl, piperazinyl or phenyl; $R^3$ is H, halo, —CN, hydroxy, $C_{1-6}$ alkyl, $C_{2-6}$ alkynyl, $C_{1-6}$ alkoxy, $C_{1-6}$ haloalkyl, —NR$^4$R$^6$, morpholinyl, piperazinyl or phenyl; Ar is phenyl, independently and optionally substituted with 1 to 4 substituents selected from the group consisting of H, $C_{1-6}$ alkyl, —OR$^4$, halo, —CN, —NO$_2$, —CO$_2$R$^4$; $R^4$, $R^5$ and $R^7$ are independently H or $C_{1-6}$ alkyl; and $R^6$ is H.

9. {3-[4-(2-Methoxybenzyloxy)-benzenesulfonyl]-6-methylpyridin-2-yl}-(4-methoxy-2-methylphenyl)-amine;
(2-Chloro-5-fluoro-4-methoxyphenyl)-{3-[4-(2-methoxybenzyloxy)-benzenesulfonyl]-6-methylpyridin-2-yl}-amine;
2-Chloro-5-fluoro-N$^1$-{3-[4-(2-methoxybenzyloxy)-benzenesulfonyl]-6-methylpyridin-2-yl}-N$^4$,N$^4$-dimethyl-benzene-1,4-diamine;
(4,5-Dimethoxy-2-methylphenyl)-{3-[4-(2-methoxybenzyloxy)-benzenesulfonyl]-6-methylpyridin-2-yl}-amine;
(2-Chloro-4-difluoromethoxyphenyl)-{3-[4-(2-methoxybenzyloxy)-benzenesulfonyl]-6-methylpyridin-2-yl}-amine;
(2-Chloro-4,5-dimethoxyphenyl)-{3-[4-(2-methoxybenzyloxy)-benzenesulfonyl]-6-methylpyridin-2-yl}-amine;
(2-Chloro-4-methanesulfonylphenyl)-{3-[4-(2-methoxybenzyloxy)-benzenesulfonyl]-6-methylpyridin-2-yl}-amine;
5-Chloro-2-{3-[4-(2-methoxybenzyloxy)-benzenesulfonyl]-6-methylpyridin-2-ylamino}-benzonitrile;
[3-(4-Methoxybenzenesulfonyl)-6-methylpyridin-2-yl]-(2,4,6-trimethylphenyl)-amine;
4-[6-Methyl-2-(2,4,6-trimethylphenylamino)-pyridine-3-sulfonyl]-phenol;
[3-(4-Benzyloxybenzenesulfonyl)-6-methylpyridin-2-yl]-(2,4,6-trimethylphenyl)-amine;
[3-(4-Ethoxybenzenesulfonyl)-6-methylpyridin-2-yl]-(2,4,6-trimethylphenyl)-amine;
[3-(4-Allyloxybenzenesulfonyl)-6-methylpyridin-2-yl]-(2,4,6-trimethylphenyl)-amine;
4-{4-[6-Methyl-2-(2,4,6-trimethylphenylamino)-pyridine-3-sulfonyl]-phenoxy}-butyronitrile;
5-{4-[6-Methyl-2-(2,4,6-trimethylphenylamino)-pyridine-3-sulfonyl]-phenoxy}-pentanenitrile;
3-{4-[6-Methyl-2-(2,4,6-trimethylphenylamino)-pyridine-3-sulfonyl]-phenoxy}-propan-1-ol;
{4-[6-Methyl-2-(2,4,6-trimethylphenylamino)-pyridine-3-sulfonyl]-phenoxy}-acetic acid ethyl ester;
2-{4-[6-Methyl-2-(2,4,6-trimethylphenylamino)-pyridine-3-sulfonyl]-phenoxy}-butyric acid methyl ester;

{6-Methyl-3-[4-(pyridin-2-ylmethoxy)-benzenesulfonyl]-pyridin-2-yl}-(2,4,6-trimethylphenyl)-amine;

{3-[4-(2,6-Dichloropyridin-4-ylmethoxy)-benzenesulfonyl]-6-methylpyridin-2-yl}-(2,4,6-trimethylphenyl)-amine;

{6-Methyl-3-[4-(2-methylthiazol-4-ylmethoxy)-benzenesulfonyl]-pyridin-2-yl}-(2,4,6-trimethylphenyl)-amine;

{3-[4-(4-Fluorobenzyloxy)-benzenesulfonyl]-6-methylpyridin-2-yl}-(2,4,6-trimethylphenyl)-amine;

4-{4-[6-Methyl-2-(2,4,6-trimethylphenylamino)-pyridine-3-sulfonyl]-phenoxymethyl}-benzonitrile;

3-{4-[6-Methyl-2-(2,4,6-trimethylphenylamino)-pyridine-3-sulfonyl]-phenoxymethyl}-benzonitrile;

3-{4-[6-Methyl-2-(2,4,6-trimethylphenylamino)-pyridine-3-sulfonyl]-phenoxymethyl}-benzoic acid methyl ester;

{3-[4-(3-Methoxybenzyloxy)-benzenesulfonyl]-6-methylpyridin-2-yl}-(2,4,6-trimethylphenyl)-amine;

{3-[4-(2-Methoxybenzyloxy)-benzenesulfonyl]-6-methylpyridin-2-yl}-(2,4,6-trimethylphenyl)-amine;

2-{4-[6-Methyl-2-(2,4,6-trimethylphenylamino)-pyridine-3-sulfonyl]-phenoxymethyl}-benzonitrile;

{6-Methyl-3-[4-(2-nitrobenzyloxy)-benzenesulfonyl]-pyridin-2-yl}-(2,4,6-trimethylphenyl)-amine;

{3-[4-(3,5-Dimethoxybenzyloxy)-benzenesulfonyl]-6-methylpyridin-2-yl}-(2,4,6-trimethylphenyl)-amine;

{3-[4-(2,5-Dimethoxybenzyloxy)-benzenesulfonyl]-6-methylpyridin-2-yl}-(2,4,6-trimethylphenyl)-amine;

{3-[4-(2,3-Dimethoxybenzyloxy)-benzenesulfonyl]-6-methylpyridin-2-yl}-(2,4,6-trimethylphenyl)-amine;

{3-[4-(2,3-Difluorobenzyloxy)-benzenesulfonyl]-6-methyl-pyridin-2-yl}-(2,4,6-trimethylphenyl)-amine;

{3-[4-(2-Fluoro-6-nitrobenzyloxy)-benzenesulfonyl]-6-methyl-pyridin-2-yl}-(2,4,6-trimethylphenyl)-amine;

1-(4-Fluoro-3-{4-[6-methyl-2-(2,4,6-trimethylphenylamino)-pyridine-3-sulfonyl]-phenoxymethyl}-phenyl)-ethanone;

{3-[4-(2,6-Dimethylbenzyloxy)-benzenesulfonyl]-6-methylpyridin-2-yl}-(2,4,6-trimethylphenyl)-amine;

[3-(3-Chloro-4-fluorobenzenesulfonyl)-6-methylpyridin-2-yl]-(2,4,6-trimethylphenyl)-amine;

[3-(3,4-Dimethylbenzenesulfonyl)-6-methylpyridin-2-yl]-(2,4,6-trimethylphenyl)-amine;

[3-(3,4-Dimethoxybenzenesulfonyl)-6-methylpyridin-2-yl]-(2,4,6-trimethylphenyl)-amine;

[3-(3,4-Dichlorobenzenesulfonyl)-6-methylpyridin-2-yl]-(2,4,6-trimethylphenyl)-amine;

[6-Methyl-3-(toluene-4-sulfonyl)-pyridin-2-yl]-(2,4,6-trimethylphenyl)-amine;

[3-(4-Ethylbenzenesulfonyl)-6-methylpyridin-2-yl]-(2,4,6-trimethylphenyl)-amine;

[3-(4-Isopropylbenzenesulfonyl)-6-methylpyridin-2-yl]-(2,4,6-trimethylphenyl)-amine;

[6-Methyl-3-(4-trifluoromethoxybenzenesulfonyl)-pyridin-2-yl]-(2,4,6-trimethylphenyl)-amine;

[3-(4-Fluorobenzenesulfonyl)-6-methylpyridin-2-yl]-(2,4,6-trimethylphenyl)-amine;

[3-(4-Bromobenzenesulfonyl)-6-methylpyridin-2-yl]-(2,4,6-trimethylphenyl)-amine;

[3-(4-Ethynylbenzenesulfonyl)-6-methylpyridin-2-yl]-(2,4,6-trimethylphenyl)-amine;

[3-(Biphenyl-4-sulfonyl)-6-methylpyridin-2-yl]-(2,4,6-trimethylphenyl)-amine;

[3-(2'-Methoxybiphenyl-4-sulfonyl)-6-methylpyridin-2-yl]-(2,4,6-trimethylphenyl)-amine;

{4-[6-Methyl-2-(2,4,6-trimethylphenylamino)-pyridine-3-sulfonyl]-phenyl}-methanol;

(6-Methyl-3-{4-[(2,4,6-trimethylphenylamino)-methyl]-benzenesulfonyl}-pyridin-2-yl)-(2,4,6-trimethylphenyl)-amine;

4-[6-Methyl-2-(2,4,6-trimethylphenylamino)-pyridine-3-sulfonyl]-benzaldehyde;

{4-[6-Methyl-2-(2,4,6-trimethylphenylamino)-pyridine-3-sulfonyl]-phenyl}-phenyl-methanol;

{4-[6-Methyl-2-(2,4,6-trimethylphenylamino)-pyridine-3-sulfonyl]-phenyl}-phenyl-methanone;

Acetic acid 4-[6-methyl-2-(2,4,6-trimethylphenylamino)-pyridine-3-sulfonyl]-benzyl ester;

[3-(3-Methoxybenzenesulfonyl)-6-methylpyridin-2-yl]-(2,4,6-trimethylphenyl)-amine;

3-[6-Methyl-2-(2,4,6-trimethylphenylamino)-pyridine-3-sulfonyl]-phenol;

[3-(3-Ethoxybenzenesulfonyl)-6-methylpyridin-2-yl]-(2,4,6-trimethylphenyl)-amine;

[3-(3-Allyloxybenzenesulfonyl)-6-methylpyridin-2-yl]-(2,4,6-trimethylphenyl)-amine;

[3-(3-Benzyloxybenzenesulfonyl)-6-methylpyridin-2-yl]-(2,4,6-trimethylphenyl)-amine;

{3-[3-(4-Fluorobenzyloxy)-benzenesulfonyl]-6-methylpyridin-2-yl}-(2,4,6-trimethylphenyl)-amine;

{3-[3-(3-Methoxybenzyloxy)-benzenesulfonyl]-6-methylpyridin-2-yl}-(2,4,6-trimethylphenyl)-amine;

{3-[3-(3,5-Dimethoxybenzyloxy)-benzenesulfonyl]-6-methylpyridin-2-yl}-(2,4,6-trimethylphenyl)-amine;

{3-[3-(6-Chloropyridin-3-ylmethoxy)-benzenesulfonyl]-6-methylpyridin-2-yl}-(2,4,6-trimethylphenyl)-amine;

{3-[3-(2,6-Dichloropyridin-4-ylmethoxy)-benzenesulfonyl]-6-methylpyridin-2-yl}-(2,4,6-trimethylphenyl)-amine;

(2,4-Dimethylphenyl)-[3-(4-ethylbenzenesulfonyl)-6-methylpyridin-2-yl]-amine;

[3-(4-Ethylbenzenesulfonyl)-6-methylpyridin-2-yl]-(4-methoxy-2-methylphenyl)-amine;

(2,4-Dimethoxyphenyl)-[3-(4-ethylbenzenesulfonyl)-6-methylpyridin-2-yl]-amine;

(2-Chloro-4-methoxyphenyl)-[3-(4-ethylbenzenesulfonyl)-6-methylpyridin-2-yl]-amine; or

[3-(4-Ethylbenzenesulfonyl)-6-methylpyridin-2-yl]-(2,4,5-trimethylphenyl)-amine or pharmaceutically acceptable salts or solvates thereof.

10. A pharmaceutical composition of a compound according to claim 1.

11. A method of treating depression or anxiety comprising a pharmaceutical composition of a compound of claim 1.

* * * * *